(12) United States Patent
Ratilainen et al.

(10) Patent No.: US 7,390,923 B2
(45) Date of Patent: Jun. 24, 2008

(54) PROPIONAMIDE DERIVATIVES USEFUL AS ANDROGEN RECEPTOR MODULATORS

(75) Inventors: Jari Ratilainen, Kulho (FI); Anu Moilanen, Turku (FI); Olli Törmäkangas, Turku (FI); Arja Karjalainen, Espoo (FI); Paavo Huhtala, Espoo (FI); Gerd Wohlfahrt, Helsinki (FI); Pekka Kallio, Turku (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 10/561,231

(22) PCT Filed: Jun. 24, 2004

(86) PCT No.: PCT/FI2004/000387

§ 371 (c)(1), (2), (4) Date: Jan. 25, 2007

(87) PCT Pub. No.: WO2005/000794

PCT Pub. Date: Jan. 6, 2005

(65) Prior Publication Data

US 2007/0123512 A1    May 31, 2007

Related U.S. Application Data

(60) Provisional application No. 60/482,713, filed on Jun. 27, 2003.

(30) Foreign Application Priority Data

Jun. 27, 2003    (FI)    .................................. 20030958

(51) Int. Cl.
C07C 233/05    (2006.01)
C07C 231/00    (2006.01)
A61K 31/16    (2006.01)

(52) U.S. Cl. ........................ 564/138; 564/142; 564/155; 564/162; 564/163; 564/164; 514/616; 514/617

(58) Field of Classification Search ........................ None
See application file for complete search history.

(56) References Cited

U.S. PATENT DOCUMENTS

| 4,636,505 A | 1/1987 | Tucker |
| 6,569,896 B2 * | 5/2003 | Dalton et al. ................ 514/493 |
| 6,838,484 B2 * | 1/2005 | Steiner et al. ................ 514/616 |
| 6,995,284 B2 * | 2/2006 | Dalton et al. ................ 564/155 |
| 2002/0099096 A1 | 7/2002 | Dalton et al. |

FOREIGN PATENT DOCUMENTS

WO    WO 03/049675 A2    6/2003
WO    WO 03/065992 A2    8/2003

OTHER PUBLICATIONS

Tucker et al. Nonsteroidal Antiandrogens. Synthesis and Structure-Activity Relationship of 3-Substituted Derivatives of 2-Hydroxypropionilides. Journal of Medicinal Chemistry, 1988, vol. 31, pp. 954-959.*
International Search Report for PCT/FI2004/000387, mailed Dec. 8, 2004.

* cited by examiner

Primary Examiner—Sikarl A Witherspoon
(74) Attorney, Agent, or Firm—Finnegan, Henderson, Farabow, Garrett & Dunner, LLP

(57) ABSTRACT

Compounds of formula (I)

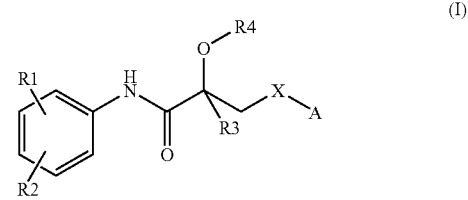

wherein R1 to R4, X and A are as defined in the claims and pharmaceutically acceptable salts and esters thereof, are disclosed. The compounds of formula (I) possess utility as tissue-selective androgen receptor modulators (SARM) and are useful in hormonal therapy, e.g., in the treatment or prevention of male hypogonadism and age-related conditions such as andropause.

11 Claims, 1 Drawing Sheet

PROPIONAMIDE DERIVATIVES USEFUL AS ANDROGEN RECEPTOR MODULATORS

This application is a U.S. national stage filing of PCT International Application No. PCT/FI2004/000387, filed on Jun. 24, 2004, which claims the benefit of priority to U.S. provisional application No. 60/482,713, filed on Jun. 27, 2003, and Finnish patent application no. 20030958, filed on Jun. 27, 2003.

TECHNICAL FIELD

The present invention relates to therapeutically active compounds and pharmaceutically acceptable salts and esters thereof useful in the treatment of nuclear receptor, especially steroid receptor, and in particular androgen receptor (AR) dependent conditions, and to pharmaceutical compositions containing such compounds. In particular, the invention discloses novel non-steroidal propionanilide structured compounds having utility as tissue-selective androgen receptor modulators (SARM). The compounds of the invention, which possess AR agonist activity, are useful in hormonal therapy, especially in treatment or prevention of conditions like male hypogonadism and age-related conditions such as andropause.

BACKGROUND OF THE INVENTION

Nuclear hormone receptors make up a family of ligand-inducible transcription factors whose members are involved in multiple physiological and developmental functions. During the last 20 years, more than sixty structurally and functionally related proteins belonging to this family have been identified. Nuclear hormone receptor family includes, in addition to classical steroid receptors (estrogen receptor, progesterone receptor, androgen receptor, glucocorticoid receptor and mineralo-corticoid receptor) also receptors e.g. for thyroid hormone, vitamin D and retinoids. Furthermore, a subclass of so-called orphan receptors for which no ligands have been identified up to date belong to this protein family. See Mangelsdorf et al, Cell (1995) 83(6): 835-839 and references therein. There exists an intense research directed to identify novel modulators for these proteins, ultimate goal thus being to find new therapies and treatment options for conditions and diseases modulated by nuclear/steroid receptors.

Steroidal androgens have been used for decades in the treatment of diseases resulting from deficiency in androgen action. They have also received attention for their use as hormone replacement therapy of aging men and in regulation of male fertility. However, current steroidal androgens, such as synthesized testosterone and its derivatives, have severe limitations. Testosterone is rapidly degraded by the liver and thus has a low systemic bioavailability after oral administration. Further, orally available testosterone formulations, e.g. methyltestosterone, have been associated with alterations in liver function. Various other attempts have been made to overcome these drawbacks of steroidal androgens as therapeutic agents, but with limited success. Current testosterone formulations used in clinical practice include e.g. injections, patches and gels.

In recent years, there has been growing interest in the development of nonsteroidal modulators for steroid receptors for therapeutical use. It has been shown that nonsteroidal ligands can achieve better receptor selectivity and better physicochemical, pharmacokinetic and pharmacological properties. For androgen receptor (AR), nonsteroidal antagonists (antiandrogens) are now used clinically to counteract the undesirable actions of excessive androgens. In contrast, nonsteroidal AR agonists, which would have potential in the treatment of diseases resulting from androgen deficiency, have just recently been reported. Still, the structural elements of nonsteroidal ligands that would lead to optimal agonist activity and tissue selectivity are poorly defined.

Non-steroidal propionanilides having androgen receptor modulating activity have been described e.g. in patent publications EP 100172, EP 253503, WO 98/53826 and WO 02/16310. The design of propionanilide structured AR modulators has concentrated on compounds where the anilide ring is substituted by two electron-withdrawing substituents such as halogen, cyano, trifluoromethyl or nitro, since such substitution has been reported to enhance the androgen receptor binding affinity of the ligand. See e.g. Tucker, H. et al., J. Med. Chem., 1988, 31, 954-959.

SUMMARY OF THE INVENTION

It has now been found that compounds of formula (I) are potent nuclear receptor modulators, in particular androgen receptor modulators. Compounds of formula (I) show remarkably high affinity and activity in androgen receptor and possess utility as tissue-selective androgen receptor modulators (SARM). Compounds of formula (I), which possess AR agonist activity, have been found to be particularly suitable for use in hormonal therapy, especially in the treatment or prevention of conditions like male hypogonadism and age-related conditions such as andropause, e.g. for providing tissue-selective androgenic or anabolic effects. For example, according to one preferred embodiment of the invention, the beneficial androgenic effects are obtained without concurrent harmful stimulation of the prostate. Compounds of the invention have generally also weak to moderate effect in the progesterone receptor, particularly antagonistic effect. It is conceived that concurrent progesterone antagonism may be beneficial as progesterone antagonism has been demonstrated to improve glucose tolerance in certain animal models. Compounds of the invention also provide good safety and sufficient water solubility.

The compounds of the present invention have a structure represented by formula (I)

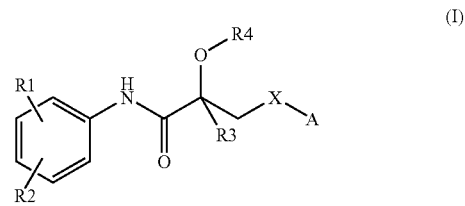

wherein $R_1$ is $(C_1$-$C_7)$alkyl, hydroxy$(C_1$-$C_7)$alkyl or —$(CH_2)_n$—CHO, wherein n is 0-6;

$R_2$ is nitro, cyano or halogen;
$R_3$ is hydrogen, $(C_1-C_7)$alkyl or halo$(C_1-C_7)$alkyl;
$R_4$ is hydrogen, $(C_1-C_7)$alkyl, $COR_{10}$ or $SO_2R_{13}$;
X is O or NH;
A is a group selected from:

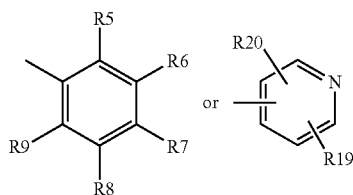

wherein $R_5$, $R_6$, $R_7$, $R_8$ and $R_9$ are independently hydrogen, halogen, nitro, cyano, $(C_1-C_7)$alkyl, halo$(C_1-C_7)$alkyl, cyano $(C_1-C_7)$alkyl, amino, mono- or di$(C_1-C_7)$alkyl-amino, amino $(C_1-C_7)$alkyl, hydroxy$(C_1-C_7)$alkyl, $(C_1-C_7)$alkoxy$(C_1-C_7)$alkyl, —$NHCOR_{10}$, —$N(COR_{10})_2$, —$COR_{11}$, —$OR_{12}$, —$OSO_2R_{13}$, —$SO_2R_{14}$, —$NHSO_2R_{13}$ or —$SR_{15}$ or an imide ring; or $R_5$ and $R_6$, $R_6$ and $R_7$, $R_7$ and $R_8$, or $R_8$ and $R_9$ form, together with any of the ring atom(s) to which they are attached, a condensed 5 to 7 membered aliphatic or aromatic carbocyclic ring or a condensed 5 to 7 membered heterocyclic ring containing 1 to 3 heteroatom(s) selected from N, O and S;

$R_{10}$ and $R_{11}$ are independently $(C_1-C_7)$alkyl, $(C_2-C_7)$alkenyl, halo$(C_1-C_7)$alkyl, amino$(C_1-C_7)$alkyl, mono- or di$(C_1-C_7)$alkylamino$(C_1-C_7)$alkyl, $(C_6-C_{10})$aryl, —$N(R_{16})_2$ or —$OR_{17}$;

$R_{12}$ and $R_{15}$ are independently hydrogen, $(C_1-C_7)$alkyl, $(C_2-C_7)$alkenyl, halo$(C_1-C_7)$alkyl, amino$(C_1-C_7)$alkyl, mono- or di$(C_1-C_7)$alkylamino$(C_1-C_7)$alkyl, $(C_6-C_{10})$aryl, —$COR_{18}$;

$R_{13}$ and $R_{14}$ are independently $(C_1-C_7)$alkyl or $(C_2-C_7)$alkenyl, halo$(C_1-C_7)$alkyl or $(C_6-C_{10})$aryl;

$R_{16}$ and $R_{17}$ are independently hydrogen, $(C_1-C_7)$alkyl, $(C_2-C_7)$alkenyl, halo$(C_1-C_7)$alkyl, amino$(C_1-C_7)$alkyl or $(C_6-C_{10})$aryl;

$R_{18}$ is $(C_1-C_7)$alkyl, $(C_2-C_7)$alkenyl, halo$(C_1-C_7)$alkyl or $(C_6-C_{10})$aryl;

$R_{19}$ and $R_{20}$ are independently hydrogen, halogen, $(C_1-C_7)$alkyl or $(C_2-C_7)$alkenyl;

and wherein each aryl or ring residue defined above may be substituted;

and pharmaceutically acceptable salts and esters thereof.

In one class of preferred compounds are compounds of formula (Ib), wherein $R_1$, $R_2$, $R_3$, $R_4$, $R_5$, $R_6$, $R_7$, $R_8$ and $R_9$ are as defined above.

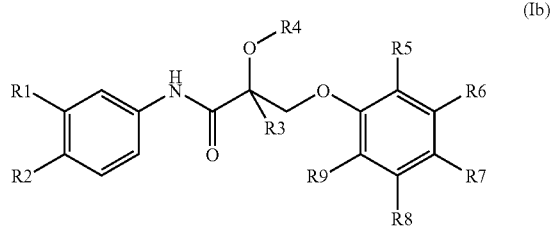

(Ib)

In another class of preferred compounds are compounds of formula (I) or (Ib), wherein $R_1$ is methyl or hydroxymethyl and $R_2$ is nitro or cyano. In another class of preferred compounds are compounds of formula (I) or (Ib) wherein $R_4$ is hydrogen and $R_3$ is methyl. In another class of preferred compounds are compounds of formula (I) or (Ib) wherein $R_5$, $R_6$, $R_7$, $R_8$ and $R_9$ are independently hydrogen, halogen, nitro, cyano, $(C_1-C_7)$alkyl, $(C_1-C_7)$alkoxy, halo$(C_1-C_7)$alkyl, hydroxy$(C_1-C_7)$alkyl or —$NHCOR_{10}$, wherein $R_{10}$ is $(C_1-C_7)$alkyl, halo$(C_1-C_7)$alkyl, hydroxy or $(C_1-C_7)$alkoxy. Particularly preferred are compounds of formula (I) or (Ib) wherein at least one of $R_5$, $R_6$, $R_7$, $R_8$ and $R_9$ is a halogen, preferably fluorine. Most preferably at least two of $R_5$, $R_6$, $R_7$, $R_8$ and $R_9$ are selected from the group consisting of halogen, preferably fluorine, cyano and acetamido. It is particularly preferred that $R_6$ is halogen, preferably fluorine.

The present invention provides further a method of hormonal therapy, comprising administering to a subject in need thereof a therapeutically effective amount of a compound of formula (I).

The present invention provides further a method for the treatment or prevention of androgen receptor (AR) dependent conditions, comprising administering to a subject in need thereof a therapeutically effective amount of a compound of formula (I).

The present invention provides further a method the treatment or prevention of androgen deficiency, comprising administering to a subject in need thereof a therapeutically effective amount of a compound of formula (I).

The present invention provides further a method the treatment or prevention of male hypogonadism and age-related conditions such as andropause, comprising administering to a subject in need thereof a therapeutically effective amount of a compound of formula (I).

The present invention also relates to a method of hormonal therapy, e.g. the treatment or prevention of androgen deficiency, comprising oral administration of compound of formula (I).

The present invention also provides a pharmaceutical composition comprising a compound of formula (I) together with a pharmaceutically acceptable carrier.

DETAILED DESCRIPTION OF THE INVENTION

Figure 1:
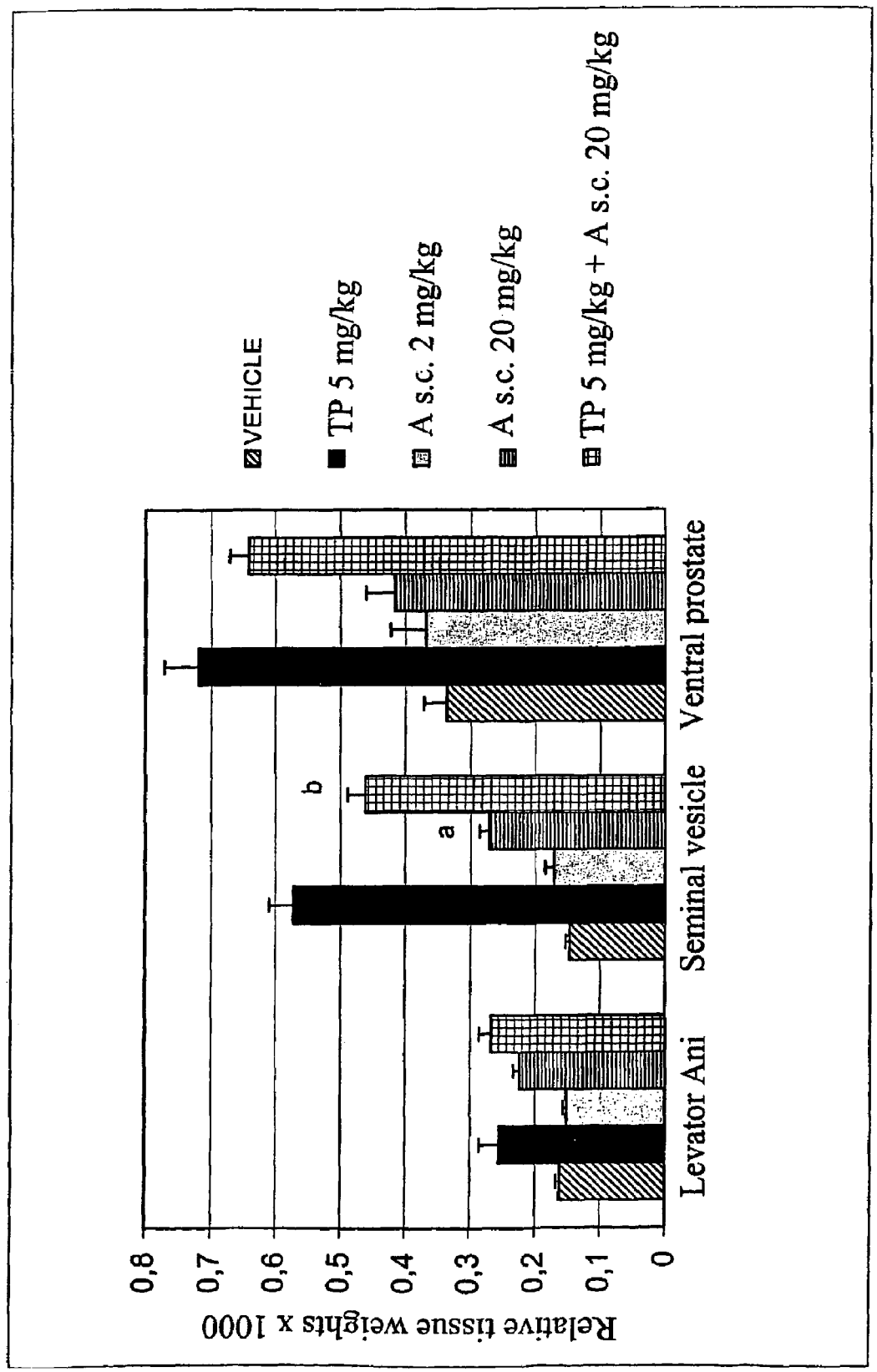
FIG. 1 shows the androgenic and anabolic activity of a compound of the invention in levator ani-muscle, seminal vesicle and ventral prostate of immature male Spraque Dawley rat.

The compounds of the invention can be prepared by a variety of synthetic routes analogously to the methods known in the literature using suitable starting materials. In particular, the compounds of the invention can be prepared analogously to the general methods described in WO 98/53826. For example, the compounds of the invention can be prepared e.g. analogously or according to the reaction Scheme 1 or 2:

Scheme 1 (Method A)
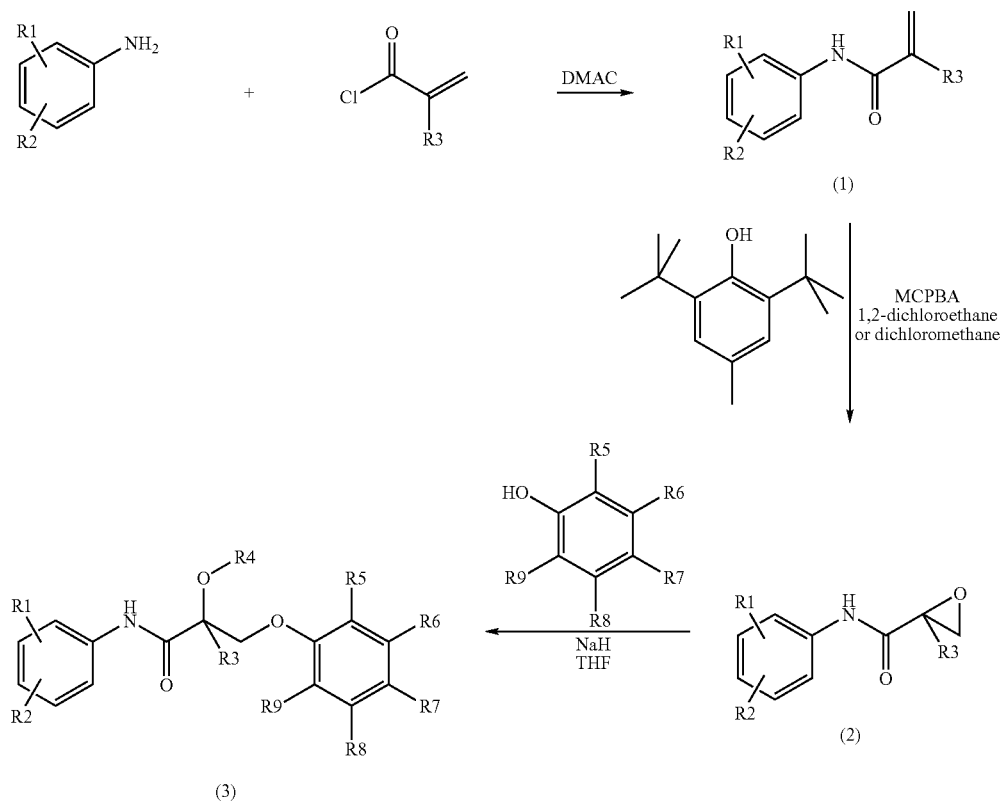
Scheme 2 (Method B)
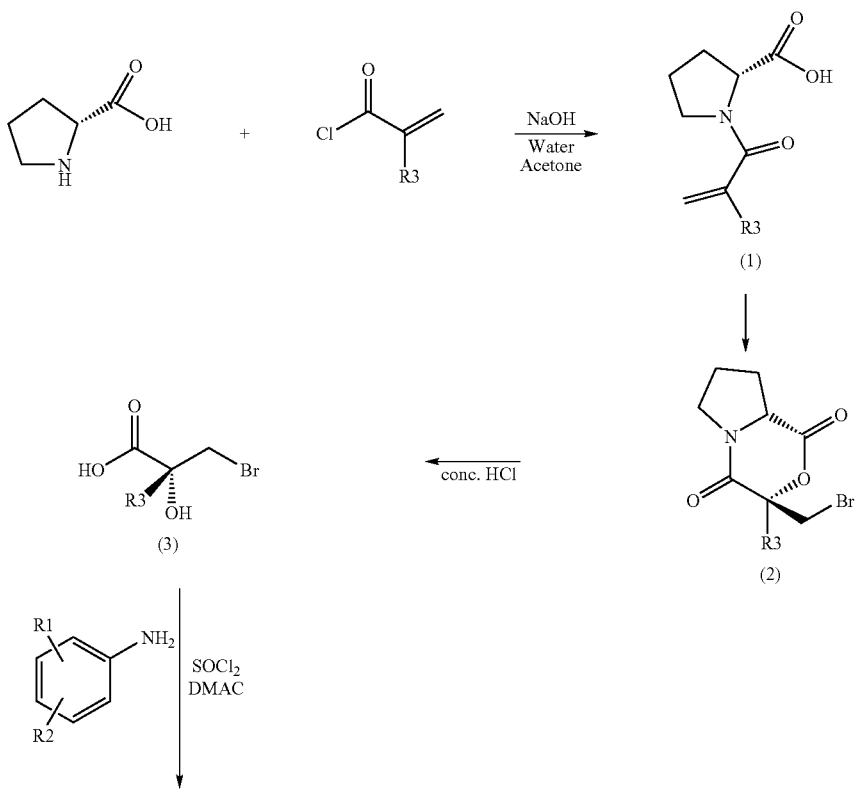

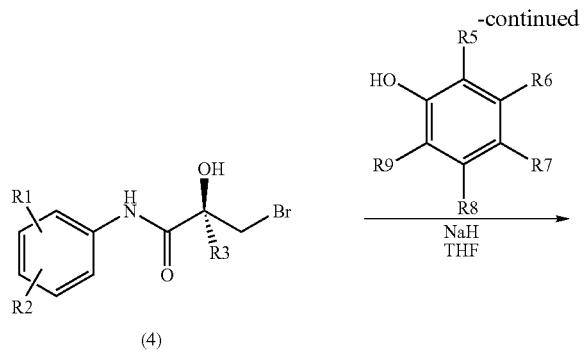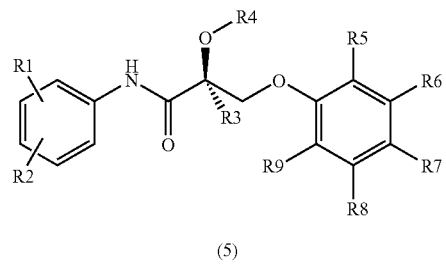

Compounds of formula (I), wherein group A is a pyridine ring or derivative thereof, can be prepared similarly as shown in Scheme 1 or 2 using suitable hydroxyl pyridine derivative in the last step. Compounds of formula (I), wherein X is —NH, can be prepared similarly as shown in Scheme 1 or 2 using suitable aniline derivative in the last step.

Pharmaceutically acceptable salts, e.g. acid addition salts with both organic and inorganic acids are well known in the field of pharmaceuticals. Non-limiting examples of these salts include chlorides, bromides, sulfates, nitrates, phosphates, sulfonates, formates, tartrates, maleates, citrates, benzoates, salicylates and ascorbates. Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols, e.g. methyl, ethyl, propyl, isopropyl, butyl, isobutyl, sec-butyl, tert-butyl esters. Phosphate esters and carbonate esters, are also within the scope of the invention.

The terms employed herein have the following meanings:

The term "halo" or "halogen", as employed herein as such or as part of another group, refers to chlorine, bromine, fluorine or iodine.

The term "($C_1$-$C_7$)alkyl", as employed herein as such or as part of another group, refers to a straight, branched or cyclized chain radical having 1 to 7 carbon atoms. Representative examples of ($C_1$-$C_7$)alkyl include, but are not limited to, methyl, ethyl, n-propyl, isopropyl, n-butyl, isobutyl, sec-butyl, tert-butyl, n-pentyl, isopentyl, neopentyl, n-hexyl, cyclopentyl, cyclohexyl and the like.

The term "($C_2$-$C_7$)alkenyl", as employed herein as such or as part of another group, refers to a straight, branched or cyclized chain radical having 2 to 7 carbon atoms, and containing (a) double bond(s).

The term "hydroxy", as employed herein as such or as part of another group, refers to an —OH group.

The term "hydroxy($C_1$-$C_7$)alkyl", as employed herein, refers to at least one hydroxy group, as defined herein, appended to the parent molecular moiety through an ($C_1$-$C_7$) alkyl group, as defined herein. Representative examples of hydroxy($C_1$-$C_7$)alkyl include, but are not limited to, hydroxymethyl, 2,2-dihydroxyethyl, 1-hydroxyethyl, 3-hydroxypropyl, 1-hydroxypropyl, 1-methyl-1-hydroxyethyl, 1-methyl-1-hydroxypropyl, and the like.

The term "halo($C_1$-$C_7$)alkyl", as employed herein, refers to at least one halogen, as defined herein, appended to the parent molecular moiety through an ($C_1$-$C_7$)alkyl group, as defined herein. Representative examples of halo($C_1$-$C_7$)alkyl include, but are not limited to, fluoromethyl, difluoromethyl, trifluoromethyl, 2-chloroethyl, 3-bromopropyl, and the like.

The term "cyano", as employed herein as such or as part of another group, refers to a —CN group.

The term "cyano($C_1$-$C_7$)alkyl", as employed herein, refers to a cyano group, as defined herein, appended to the parent molecular moiety through an ($C_1$-$C_7$)alkyl group, as defined herein. Representative examples of cyano($C_1$-$C_7$)alkyl include, but are not limited to, cyanomethyl, 1-cyanoethyl, 1-cyanopropyl, 2-cyanopropyl, and the like.

The term "amino", as employed herein as such or as part of another group, refers to a —$NH_2$ group.

The term "amino($C_1$-$C_7$)alkyl", as employed herein, refers to at least one amino group, as defined herein, appended to the parent molecular moiety through an ($C_1$-$C_7$)alkyl group, as defined herein. Representative examples of amino($C_1$-$C_7$) alkyl include, but are not limited to, aminomethyl, 2-aminoethyl, 1-aminoethyl, 2,2-diaminoethyl, 3-aminopropyl, 2-aminopropyl, 4-aminobutyl, 1-methyl-1-aminoethyl, and the like.

The term "mono- or di($C_1$-$C_7$)alkylamino", as employed herein as such or as part of another group, refers to one or two ($C_1$-$C_7$)alkyl group(s), as defined herein, appended to the parent molecular moiety through an amino group, as defined herein. Representative examples of mono- or di($C_1$-$C_7$)alkylamino include, but are not limited to methylamino, ethylamino, propylamino, butylamino, dimethylamino, diethylamino, N-ethyl-N-methylamino, and the like.

The term "mono- or di($C_1$-$C_7$)alkylamino($C_1$-$C_7$)alkyl", as employed herein, refers to a mono- or di($C_1$-$C_7$)alkylamino group, as defined herein, appended to the parent molecular moiety through a ($C_1$-$C_7$)alkyl group, as defined herein. Representative examples of mono- or di($C_1$-$C_7$)alkylamino($C_1$-$C_7$)alkyl include, but are not limited to, N,N-dimethylaminomethyl, N,N-diethylaminomethyl, N-methylaminoethyl, N-methylaminopropyl, N-ethyl-N-methylaminomethyl, and the like.

The term "($C_1$-$C_7$)alkoxy", as employed herein as such or as part of another group, refers to —O—($C_1$-$C_7$)alkyl, wherein —($C_1$-$C_7$)alkyl is as defined herein. Representative examples of ($C_1$-$C_7$)alkoxy include, but are not limited to methoxy, ethoxy, propoxy, butoxy, isobutoxy, sec-butoxy, tert-butoxy, and the like.

The term "($C_1$-$C_7$)alkoxy($C_1$-$C_7$)alkyl", as employed herein, refers to at least one ($C_1$-$C_7$)alkoxy group, as defined herein, appended to the parent molecular moiety through an ($C_1$-$C_7$)alkyl group, as defined herein. Representative examples of ($C_1$-$C_7$)alkoxy($C_1$-$C_7$)alkyl include, but are not limited to methoxymethyl, ethoxymethyl, 2-methoxyethyl, 2-ethoxyethyl, 3,3-dimethoxypropyl, 2,4-dimethoxybutyl and the like.

The term "$(C_6-C_{10})$aryl" as employed herein by itself or as part of another group refers to a monocyclic or bicyclic group containing 6 to 10 carbon atoms in the ring portion. Representative examples of $(C_6-C_{10})$aryl include, but are not limited to phenyl, naphtyl and the like.

The term "$(C_2-C_7)$acyl" as employed herein by itself or as part of another group refers to alkylcarbonyl or alkenylcarbonyl group having 2 to 7 carbon atoms, and examples thereof include acetyl, propanoyl, isopropanoyl, butanoyl, sec-butanoyl, tert-butanoyl and pentanoyl.

The term "substituted" as used herein in connection with various residues refers to halogen substituents, such as fluorine, chlorine, bromine, iodine, or $(C_1-C_7)$alkyl, halo$(C_1-C_7)$alkyl, hydroxy, amino, $(C_1-C_7)$alkoxy, $(C_2-C_7)$acyl $(C_1-C_7)$alkylamino, amino$(C_1-C_7)$alkyl, nitro, cyano, or thiol substituents.

The "substituted" groups may contain 1 to 3, preferably 1 or 2, most preferably 1 of the above mentioned substituents.

The definition of formula (I) above is inclusive of all the possible stereo-isomers of the compounds, including geometric isomers, e.g. Z and E isomers (cis and trans isomers), and optical isomers, e.g. diastereomers and enantiomers, and all prodrugesters, e.g. phosphate esters and carbonate esters. Furthermore, the invention includes in its scope both the individual isomers and any mixtures thereof, e.g. racemic mixtures. The individual isomers may be obtained using the corresponding isomeric forms of the starting material or they may be separated after the preparation of the end compound according to conventional separation methods. For the separation of optical isomers, e.g. enantiomers, from the mixture thereof the conventional resolution methods, e.g. fractional crystallisation, may be used.

Examples of preferred compounds of formula (I) include
3-(4-Acetylamino-3-fluorophenoxy)-2-hydroxy-2-methyl-N-(3-methyl-4-nitrophenyl)propionamide;
(2S)-3-(4-Acetylamino-3-fluorophenoxy)-2-hydroxy-2-methyl-N-(3-methyl-4-nitrophenyl)propionamide;
3-(4-Acetylaminophenoxy)-2-hydroxy-2-methyl-N-(3-methyl-4-nitrophenyl)propionamide;
(2S)-3-(4-Acetylaminophenoxy)-2-hydroxy-2-methyl-N-(3-methyl-4-nitrophenyl)propionamide;
3-(3-Chloro-4-fluorophenoxy)-2-hydroxy-2-methyl-N-(3-methyl-4-nitrophenyl)propionamide;
3-(4-Cyanophenoxy)-2-hydroxy-2-methyl-N-(3-methyl-4-nitrophenyl)propionamide;
3-(2-Fluorophenoxy)-2-hydroxy-2-methyl-N-(3-methyl-4-nitrophenyl)propionamide;
3-(3-Fluorophenoxy)-2-hydroxy-2-methyl-N-(3-methyl-4-nitrophenyl)propionamide;
3-(3-Chloro-4-fluorophenoxy)-2-hydroxy-2-methyl-N-(3-methyl-4-nitrophenyl)propionamide;
3-(3,4-Difluorophenoxy)-2-hydroxy-2-methyl-N-(3-methyl-4-nitrophenyl)propionamide;
3-(4-Chlorophenoxy)-2-hydroxy-2-methyl-N-(3-methyl-4-nitrophenyl)propionamide;
2-Hydroxy-3-(4-methoxyphenoxy)-2-methyl-N-(3-methyl-4-nitrophenyl)propionamide;
3-(2,4-Dichloro-3,5-dimethylphenoxy)-2-hydroxy-2-methyl-N-(3-methyl-4-nitrophenyl)propionamide;
3-(4-Chloro-3-nitrophenoxy)-2-hydroxy-2-methyl-N-(3-methyl-4-nitrophenyl)propionamide;
3-(4-Cyano-3-fluoro-phenoxy)-2-hydroxy-2-methyl-N-(3-methyl-4-nitrophenyl)propionamide;
3-(4-Fluorophenylamino)-2-hydroxy-2-methyl-N-(3-methyl-4-nitrophenyl)propionamide;
3-[4-(3-Chloropropyl)phenoxy]-2-hydroxy-2-methyl-N-(3-methyl-4-nitrophenyl)propionamide;
2-Hydroxy-3-(4-methoxymethylphenoxy)-2-methyl-N-(3-methyl-4-nitrophenyl)propionamide;
2-Hydroxy-2-methyl-N-(3-methyl-4-nitrophenyl)-3-(pyridin-4-yloxo)propionamide;
3-[4-(2-Chloroethoxy)phenoxy]-2-hydroxy-2-methyl-N-(3-methyl-4-nitrophenyl)propionamide;
{2-Fluoro-4-[2-hydroxy-2-(3-methyl-4-nitrophenylcarbamoyl)propoxy]-phenyl}carbamic acid ethyl ester;
3-(4-Cyanophenylamino)-2-hydroxy-2-methyl-N-(3-methyl-4-nitrophenyl)propionamide;
(2S)-3-(4-Cyano-3-fluoro-phenoxy)-2-hydroxy-2-methyl-N-(3-methyl-4-nitrophenyl)propionamide;
3-(3-Chloro-4-cyanophenylamino)-2-hydroxy-2-methyl-N-(3-methyl-4-nitrophenyl)propionamide;
3-[4-(2-Bromoethyl)phenoxy]-2-hydroxy-2-methyl-N-(3-methyl-4-nitrophenyl)propionamide;
3-(4-Cyano-3-fluorophenoxy)-N-(3-ethyl-4-nitrophenyl)-2-hydroxy-2-methylpropionamide; and
3-(3-Chloro-4-cyanophenoxy)-2-hydroxy-2-methyl-N-(3-methyl-4-nitrophenyl)propionamide.

Compounds of the invention may be administered to a patient in therapeutically effective amounts which range usually from about 0.1 to about 1000 mg per day depending on the age, weight, ethnic group, condition of the patient, condition to be treated, administration route and the androgen (AR) modulator used. The compounds of the invention can be formulated into dosage forms using the principles known in the art. It can be given to a patient as such or in combination with suitable pharmaceutical excipients in the form of tablets, granules, capsules, suppositories, emulsions, suspensions or solutions. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds and other ingredients normally used in this field of technology may be also used. The compositions containing the active compound can be given enterally or parenterally, the oral route being the preferred way. The contents of the active compound in the composition is from about 0.5 to 100%, preferably from about 0.5 to about 20%, per weight of the total composition.

The present invention will be explained in more detail by the following examples. The examples are meant only for illustrating purposes and do not limit the scope of the invention defined in claims.

EXPERIMENTS

Experiment 1

AR Binding Assay

Ventral prostates were obtained form rats castrated 24 h prior to sacrifice. Fresh prostate was minced and washed with Buffer A (Schilling and Liao, Prostate, 5:581-588, 1984). The minces were then homogenized in 3× volume of Buffer A containing protease inhibitors (Complete, Mini, EDTA-free Roche). The homogenate was centrifuged at 30000 g for 30 min. The resultant supernatants were treated with 1×volume of dextran-coated charcoal solution (12.5 g activated charcoal, 12.5 g dextran per liter of buffer A) to remove endogenous steroids. The samples were incubated for 5 min and centrifuged at 16000 g for 10 min. Aliquots of the charcoal-treated cytosol were taken for androgen receptor assays. All procedures were carried out at 0-4° C.

Cytosol androgen receptor concentration was determined as described (Isomaa et al., Endocrinology, 111: 833-843, 1982) with minor modifications. Cytosol preparations were prepared as described above, and bound and free steroids were separated by treatment with an equal volume of dextran-charcoal suspension for 5 min at 4° C. followed by centrifugation at 16000 g for 10 min. Bound radioactivity was determined by counting supernatant fractions in 1 ml of OptiPhase HiSafe3 or OptiPhase Supermix (PerkinElmer).

Cytosol preparations were labelled with 1 nM [$^3$H]-mibolerone overnight at 0° C. (total). To determine AR binding activity of the compounds of the present invention (test compounds), the ability of test compounds to compete with [$^3$H] 7α,17α-dimethyl-17β-hydroxy-4-estren-3-one ([$^3$H]-mibolerone) binding was studied. 1 nM [$^3$H]-mibolerone and test compounds in two concentrations (0.2 and 2 uM) were incubated overnight at 0° C. To determine non-specific binding, parallel incubations were carried out using 1 nM concentration [$^3$H]-mibolerone with 500-fold molar excess of unlabelled testosterone. Two to four replicates were used for each sample. After incubation, bound and free steroids were separated as described above and bound radioactivity was determined. The ability of the test compounds to bind AR is reported as reduction in bound radioactivity obtained with 1 nM [$^3$H]-mibolerone. The results are shown in Table 1. The results (% inhibition) were calculated as: % inhibition=100−(100×(average$_{test\ compound}$/average$_{total}$)).

TABLE 1

AR binding assay. Inhibition (%) of [3H]-mibolerone binding.

| Compound of Example No. | Inhibition (%) of [3H]-mibolerone binding at 0.2 μM | Inhibition (%) of [3H]-mibolerone binding at 2.0 μM |
| --- | --- | --- |
| 1. | 91 | 101 |
| 2. | 93 | 100 |
| 3. | 103 | 115 |
| 4. | 90 | 88 |
| 5. | 25 | 74 |
| 6. | 68 | 95 |
| 7. | 74 | 98 |
| 8. | 93 | 109 |
| 9. | 41 | 102 |
| 10. | 5 | 83 |
| 11. | 98 | 105 |
| 12. | 77 | 101 |
| 13. | 77 | 90 |
| 14. | 75 | 95 |
| 15. | 46 | 77 |
| 16. | 50 | 91 |
| 17. | 95 | 98 |
| 18. | 90 | 99 |
| 19. | 83 | 99 |
| 20. | 13 | 83 |
| 21. | 26 | 91 |
| 23. | 88 | 92 |
| 24. | 75 | 93 |
| 25. | 96 | 98 |
| 26. | 62 | 92 |
| 27. | 34 | 89 |
| 28. | 90 | 88 |
| 29. | 92 | 90 |
| 30. | 80 | 99 |
| 31. | 18 | 75 |
| 36. | 3 | 50 |
| 42. | 83 | 97 |
| 43. | 95 | 99 |
| 44. | 83 | 100 |
| 50. | 96 | 99 |
| 51. | 73 | 92 |

TABLE 1-continued

AR binding assay. Inhibition (%) of [3H]-mibolerone binding.

| Compound of Example No. | Inhibition (%) of [3H]-mibolerone binding at 0.2 μM | Inhibition (%) of [3H]-mibolerone binding at 2.0 μM |
| --- | --- | --- |
| 52. | 90 | 115 |
| 55. | 87 | 99 |
| 56. | 90 | 95 |
| 58. | 84 | 93 |
| 63. | 92 | 98 |
| 64. | 79 | 89 |
| 66. | 69 | 93 |
| 79. | 89 | 98 |
| 80. | 87 | 99 |
| 81. | 85 | 98 |

Experiment 2

Ar Agonism and Antagonism in Immature Male Rats

The title compound of Example 3, abbreviated here as compound A, was further studied in in vivo experiment. The agonism and antagonism of the compound with subcutaneous dosing was tested in immature male Spraque Dawley rat 3-day assay by analyzing the relative weights of ventral prostate, seminal vesicle, and levator ani-muscle. Testosterone propionate was used as a reference compound.

Testosterone propionate (abbreviated here TP) and compound A were first dissolved into DMSO and then into the vehicle sesame oil. Sprague-Dawley untreated male rats (18-19 days old) weighing about 50 g were used in the experiment. Rats were weighed and randomly distributed into five groups, with 5 animals per group (Table 1). Compound A (doses 2 and 20 mg/kg) and testosterone propionate (dose 5 mg/kg) were given subcutaneously (s.c.) into the neck/back of the animals at a constant volume of 100 microl dosing solution/animal/day. The animals were dosed once daily for three days, and clinical signs were recorded during dosing. At the end of the study, animals were weighed and anaesthetised by $CO_2$ asphyxiation. Ventral prostate, seminal vesicles, and levator ani-muscle were dissected out, chilled, and weighed. For statistical analysis, the weights of all organs were normalized to body weights, and analyzed for statistical significant difference by single-factor ANOVA.

TABLE 2

Animal groups and experimental design

| Dose group & group number | Number of animals |
| --- | --- |
| 1. Vehicle | 5 |
| 2. Testosterone propionate (TP) 5 mg/kg s.c. | 5 |
| 3. Compound A, 2 mg/kg | 5 |
| 4. Compound A, 20 mg/kg | 5 |
| 5. TP 5 mg/kg + Compound A, 20 mg/kg s.c. | 5 |

The results are shown in FIG. 1. Compound A shows androgenic and anabolic activity. The relative weights of ventral prostate, seminal vesicle and levator ani-muscle increased significantly with administration of testosterone propionate. Compared with testosterone propionate, compound A showed tissue selectivity. At dose 20 mg/kg it clearly increased the relative weight of levator ani-muscle and significantly the relative weight of seminal vesicle, but only minimally the relative weight of the prostate. Furthermore, compound A showed significant antagonistic activity in seminal vesicle. Neither testosterone propionate nor compound A had any effect on the body weights (data not shown). In the Figure, "a" means agonism, p<0.01 compared to vehicle group, "b" means antagonism, p<0.05 compared to testosterone group, bars represent mean±SEM.

EXAMPLES

Example 1

Method A 3-(4-Acetylaminophenoxy)-2-hydroxy-2-methyl-N-(3-methyl-4-nitrophenyl)propionamide a) 2-Methyl-N-(3-methyl-4-nitrophenyl)acrylamide 3-Methyl-4-nitroaniline (2.0 g, 13 mmol) in N,N-dimethylacetamide (DMAC) (6 ml) was added dropwise to a cooled solution of methacryloyl chloride (2.0 ml, 20.7 mmol) in a nitrogen atmosphere while the temperature of the reaction mixture was maintained between 0-5° C. The solution was allowed to warm to room temperature and the mixture was stirred over night. The mixture was poured into water (70 ml) and extracted with ethyl acetate (4×40 ml). The organic phase was washed with saturated $Na_2CO_3$ (3×20 ml) and water (1×50 ml), dried over $Na_2SO_4$ and evaporated. The yield of the crude product was 4.17 g (contains DMA, theoretical yield 2.9 g), and it was used without further purifications. $^1$H NMR (DMSO-$d_6$): 1.97 (3H, s), 2.55 (3H, s), 5.62 (1H, m), 5.96 (1H, m), 7.80 (2H, m), 8.05 (1H, m), 10.22 (1H, s).

b) 2-Methyloxirane-2-carboxylic acid (3-methyl-4-nitrophenyl)amide m-Chloroperoxybenzoic acid (6.7 g, 29.9 mmol) was added in portions at 60° C. to a solution of 2-methyl-N-(3-methyl-4-nitrophenyl)acrylamide (2.9 g, 13.2 mmol) and 2,6-di-tert-butyl-4-methylphenol (66 mg) in 1,2-dichloroethane (80 ml). The string was continued at 60° C. for 6 h, and the reaction mixture was allowed to cool to room temperature. The precipitated m-chlorobenzoic acid was filtered, and the filtrate was extracted with 1 M $Na_2CO_3$ (4×60 ml). The organic phase was dried over $Na_2SO_4$ and evaporated. The yield was 3.05 g. $^1$H NMR (DMSO-$d_6$): 1.54 (3H, s), 2.51 (3H, s), 2.99 (1H, d, J=5.1 Hz), 3.05 (1H, d, J=5.1 Hz), 7.79 (2H, m), 8.01 (1H, m), 9.98 (1H, s).

c) 3-(4-Acetylaminophenoxy)-2-hydroxy-2-methyl-N-(3-methyl-4-nitrophenyl)propionamide A solution of 4-acetamidophenol (2.9 g, 19 mmol) in THF (60 ml) was added dropwise to a stirred suspension of sodium hydride (0.46 g, 19 mmol, 60% dispersion in mineral oil) in THF (60 ml) and the temperature was kept below 5° C. during the addition. The mixture was stirred for 10 min and a solution of 2-methyl-oxirane-2-carboxylic acid (3-methyl-4-nitrophenyl)amide (3.05 g, 13 mmol) in THF (120 ml) was added. The mixture was heated to 60° C. and stirred at this temperature for 7 h, and allowed to cool to the room temperature. The solvent was evaporated and the residue was dissolved to the mixture of water (150 ml) and ethyl acetate (150 ml). The pH was adjusted to 2-3 with 2 M HCl and the phases were separated. The aqueous phase was extracted with ethyl acetate (4×150 ml). The combined organic phase was washed with 1 M $Na_2CO_3$ (5×100 ml), dried over $Na_2SO_4$ and evaporated. The oily residue was crystallised from the mixture of ethyl acetate-diethyl ether (10:1). The crude product was recrystallised from ethyl acetate. The yield was 2.5 g. $^1$H NMR (DMSO-$d_6$): 1.42 (3H, s), 1.99 (3H, s), 2.53 (3H, s), 3.93 (1H, d, J=9.6 Hz), 4.16 (1H, d, J=9.6 Hz), 6.20 (1H, bs), 6.84 (2H, d, J=9.0 Hz), 7.44 (2H, d, J=9.0 Hz), 7.88 (1H, dd, J=9.0 Hz and 2.3 Hz), 7.93 (1H, d, J=2.3 Hz), 8.04 (1H, d, J=9.0 Hz), 9.76 (1H, s), 10.15 (1H, bs).

Example 2

3-(4-Acetylamino-3-fluorophenoxy)-2-hydroxy-2-methyl-N-(3-methyl-4-nitrophenyl)propionamide a) N-(2-Fluoro-4-hydroxyphenyl)acetamide Acetic anhydride (1.3 ml, 13.8 mmol) was added dropwise to a solution of 4-amino-3-fluorophenol (1.0 g, 7.9 mmol) in acetic acid (25 ml) at room temperature. The reaction mixture was stirred at room temperature for 2 h and water (2 ml) was added and the stirring was continued for 30 minutes at room temperature. The mixture was evaporated to dryness in vacuo. The yield of the crude product was 1.3 g (100%) and it was used without further purification.

$^1$H NMR (DMSO-$d_6$): 2.00 (3H, s), 6.50-6.68 (2H, m), 7.39 (1H, m), 9.39 (1H, s), 9.72 (1H, s).

b) 3-(4-Acetylamino-3-fluorophenoxy)-2-hydroxy-2-methyl-N-(3-methyl-4-nitrophenyl)propionamide The compound was synthesised according to the procedure described in Example 1c. N-(2-Fluoro-4-hydroxyphenyl)acetamide (0.5 g, 3.0 mmol) and 2-methyloxirane-2-carboxylic acid (3-methyl-4-nitrophenyl)amide (0.6 g, 2.5 mmol) was used as starting materials. The product was crystallised from the mixture of ethyl acetate and diethyl ether (1:1). The yield was 0.39 g. $^1$H NMR (DMSO-$d_6$): 1.42 (3H, s), 2.02 (3H, s), 2.53 (3H, s), 3.97 (1H, d, J=9.7 Hz), 4.21 (1H, d, J=9.7 Hz), 6.23 (1H, bs), 6.72 (1H, m), 6.90 (1H, m), 7.56 (1H, m), 7.88 (1H, dd, J=9.0 Hz and 2.2 Hz), 7.93 (1H, d, J=2.2 Hz), 8.03 (1H, d, J=9.0 Hz), 9.51 (1H, s), 10.15 (1H, bs).

Example 3

Method B (2S)-3-(4-Acetylaminophenoxy)-2-hydroxy-2-methyl-N-(3-methyl-4-nitrophenyl)propionamide a) (2R)-1-(2-Methylacryloyl)pyrrolidine-2-carboxylic acid D-proline (5 g, 43.4 mmol) was dissolved in 2 M NaOH (26 ml) and cooled in an ice bath, and the solution was diluted with acetone (26 ml). An acetone solution (26 ml) of methacryloyl chloride (6.3 ml, 65.1 mmol) and a 2 M NaOH solution (34 ml) were simultaneously added over a period of 1 h to the solution of D-proline. After addition the resulting mixture was stirred for 3 h at room temperature. The mixture was evaporated at 40° C., extracted with ether (2×40 ml) and acidified to pH 2 with concentrated HCl. The resulting mixture was extracted with ethyl acetate (3×50 ml), dried over $Na_2SO_4$ and evaporated. The yield was 11.5 g (theoretical 8.0 g), and it was used without further purifications.

b) (3R,8aR)-3-Bromomethyl-3-methyltetrahydropyrrolo[2,1-c][1,4]oxazine-1,4-dione NBS (16 g, 89.9 mmol) was dissolved in DMF (50 ml) and added at room temperature to a solution of (2R)-1-(2-methylacryloyl)pyrrolidine-2-carboxylic acid (11.5 g, contains 8.0 g of the corresponding starting material, 43.4 mmol) in DMF (50 ml). The mixture was stirred for 20 h and evaporated at 80-90° C. The residue was mixed with water (250 ml) and extracted with ethyl acetate (4×80 ml). The combined ethyl acetate phases were washed with 1 M NaHCO$_3$ solution (2×50 ml) and water (1×50 ml). The organic phase was dried over Na$_2$SO$_4$ and evaporated. The yield of the crude oil was 9.3 g. Ethyl acetate (10 ml) was added and the mixture was stirred in an ice bath. The precipitated product was filtered and washed with cooled ethyl acetate. The yield was 1.2 g. $^1$H NMR (DMSO-d$_6$): 1.58 (3H, s), 1.75-2.10 (3H, m), 2.25 (1H, m), 3.30-3.55 (2H, m), 3.87 (1H, d, J=11.4 Hz), 4.03 (1H, d, J=11.4 Hz), 4.70 (1H, m).

c) (2R)-3-Bromo-2-hydroxy-2-methylpropionic acid (3R,8aR)-3-Bromomethyl-3-methyltetrahydropyrrolo[2,1-c][1,4]oxazine-1,4-dione (1.1 g, 4.2 mmol) was dissolved in concentrated HCl (10 ml) and refluxed for 7 h. The mixture was cooled to room temperature. Water (20 ml) was added and the mixture was extracted with ethyl acetate (3×20 ml). The combined organic phase was evaporated and the residue was mixed with toluene (5 ml). The crystallised product was filtered and washed with toluene. The yield was 0.74 g. $^1$H NMR (DMSO-d$_6$): 1.37 (3H, s), 3.54 (1H, d, J=10.2 Hz), 3.64 (1H, d, J=10.2 Hz), 5.35 (1H, bs), 12.80 (1H, bs).

d) (2R)-3-Bromo-2-hydroxy-2-methyl-N-(3-methyl-4-nitrophenyl)propionamide

Thionyl chloride (0.48 ml, 6.6 mmol) was added dropwise to a solution of (2R)-3-Bromo-2-hydroxy-2-methylpropionic acid (1.0 g, 5.5 mmol) in 10 ml of DMA at −5 to −10° C. The mixture was stirred for 2 h, and a solution of 3-methyl-4-nitroaniline (0.83 g, 5.5 mmol) in 7 ml of DMA was added to the above mixture. The resulting mixture was stirred for 3 h at room temperature and poured into water (250 ml). The aqueous phase was extracted with ethyl acetate (4×50 ml), dried over Na$_2$SO$_4$ and evaporated. The yield of the desired compound was 2.5 g (contains also DMA), and it was used without further purifications. $^1$H NMR (DMSO-d$_6$): 1.48 (3H, s), 2.53 (3H, s), 3.58 (1H, d, J=10.4 Hz), 3.82 (1H, d, J=10.4 Hz), 6.34 (1H, bs), 7.86 (1H, dd, J=9.0 Hz and 2.2 Hz), 7.91 (1H, d, J=2.2 Hz), 8.04 (1H, d, J=9.0 Hz), 10.09 (1H, bs).

e) (2S)-3-(4-Acetylaminophenoxy)-2-hydroxy-2-methyl-N-(3-methyl-4-nitrophenyl)propionamide A solution of 4-acetamidophenol 0.62 g, 4.1 mmol) in THF (7 ml) was added dropwise to a stirred suspension of sodium hydride (0.27 g, 6.8 mmol, 60% dispersion in mineral oil) in THF (6 ml) and the temperature was kept below 5° C. during the addition. The mixture was stirred for 10 min and a solution of (2R)-3-bromo-2-hydroxy-2-methyl-N-(3-methyl-4-nitrophenyl)propionamide (0.86 g, 2.7 mmol) in THF (7 ml) was added. The mixture was stirred at room temperature for 30 min and then at 60° C. for 5 h, and allowed to cool to the room temperature. The solvent was evaporated and the residue was dissolved to the mixture of water (80 ml) and ethyl acetate (80 ml). The pH was adjusted to 2-3 with 2 M HCl and the phases were separated. The organic phase was washed with 1 M Na$_2$CO$_3$ (6×30 ml), dried over Na$_2$SO$_4$ and evaporated. The oily residue was crystallised from ethyl acetate. The yield was 0.27 g. $^1$H NMR (DMSO-d$_6$): 1.42 (3H, s), 1.99 (3H, s), 2.53 (3H, s), 3.93 (1H, d, J=9.6 Hz), 4.16 (1H, d, J=9.6 Hz), 6.20 (1H, bs), 6.84 (2H, d, J=9.0 Hz), 7.44 (2H, d, J=9.0 Hz), 7.88 (1H, dd, J=9.0 Hz and 2.3 Hz), 7.93 (1H, d, J=2.3 Hz), 8.04 (1H, d, J=9.0 Hz), 9.76 (1H, s), 10.15 (1H, bs).

Example 4

(2S)-3-(4-Acetylamino-3-fluorophenoxy)-2-hydroxy-2-methyl-N-(3-methyl-4-nitrophenyl)propionamide (2S)-3-(4-Acetylamino-3-fluorophenoxy)-2-hydroxy-2-methyl-N-(3-methyl-4-nitrophenyl)propionamide was prepared according to the method B as described in Example 3e starting from 4-acetylamino-3-fluorophenol and N-[3-methyl-4-(nitro)phenyl]-(2R)-3-bromo-2-hydroxy-2-methyl-propanamide. $^1$H NMR (DMSO-d$_6$): 1.42 (3H, s), 2.02 (3H, s), 2.53 (3H, s), 3.97 (1H, d, J=9.7 Hz), 4.21 (1H, d, J=9.7 Hz), 6.23 (1H, bs), 6.72 (1H, m), 6.90 (1H, m), 7.56 (1H, m), 7.88 (1H, dd, J=9.0 Hz and 2.2 Hz), 7.93 (1H, d, J=2.2 Hz), 8.03 (1H, d, J=9.0 Hz), 9.51 (1H, s), 10.15 (1H, bs).

Example 5

4-[2-Hydroxy-2-(3-methyl-4-nitrophenylcarbamoyl)propoxy]benzamide

4-[2-Hydroxy-2-(3-methyl-4-nitrophenylcarbamoyl)propoxy]benzamide was prepared as described in Example 1 starting from 4-hydroxybenzamide and 1,2-epoxy-2-methyl-N-(3-methyl-4-nitrophenyl)-2-propanamide. $^1$H NMR (400 MHz, DMSO-d$_6$): 1.45 (3H, s), 2.53 (3H, s), 4.04 (1H, d, J=9.7 Hz), 4.28 (1H, d, J=9.7 Hz), 6.26 (1H, s), 6.94-6.98 (2H, m), 7.19 (1H, br s), 7.80-7.83 (3H, m), 7.89 (1H, dd, J=9.0 Hz, J=2.2 Hz), 7.95 (1H, d, J=2.0 Hz), 8.05 (1H, d, J=9.0 Hz), 10.19 (1H, s).

Example 6

3-(3,4-Dichlorophenoxy)-2-hydroxy-2-methyl-N-(3-methyl-4-nitrophenyl)propionamide 3-(3,4-Dichlorophenoxy)-2-hydroxy-2-methyl-N-(3-methyl-4-nitrophenyl)propionamide was prepared as described in Example 1 starting from 3,4-dichlorophenol and 1,2-epoxy-2-methyl-N-(3-methyl-4-nitrophenyl)-2-propanamide.

$^1$H NMR (400 MHz, DMSO-d$_6$): 1.43 (3H, s), 2.53 (3H, s), 4.02 (1H, d, J=9.9 Hz), 4.28 (1H, d, J=9.9 Hz), 6.27 (1H, s), 6.95 (1H, dd, J=8.9 Hz, J=2.8 Hz), 7.25 (1H, d, J=2.8 Hz), 7.49 (1H, d, J=8.9 Hz), 7.88 (1H, dd, J=9.0 Hz, J=2.3 Hz), 7.93 (1H, d, J=2.0 Hz), 8.04 (1H, d, J=9.0 Hz), 10.17 (1H, s).

Example 7

4-[2-Hydroxy-2-(3-methyl-4-nitrophenylcarbamoyl)propoxy]benzoic acid ethyl ester 4-[2-Hydroxy-2-(3-methyl-4-nitrophenylcarbamoyl)propoxy]benzoic acid ethyl ester was prepared as described in Example 1 starting from ethyl 4-hydroxy-benzoate and 1,2-epoxy-2-methyl-N-(3-methyl-4-nitrophenyl)-2-propanamide.

$^1$H NMR (400 MHz, DMSO-d$_6$): 1.30 (3H, t, J=7.1 Hz), 1.45 (3H, s), 2.53 (3H, s), 4.07 (1H, d, J=9.7 Hz), 4.26 (2H, q,

J=7.1 Hz), 4.30 (1H, d, J=9.7 Hz), 6.29 (1H, s), 7.01-7.05 (2H, m), 7.86-7.91 (3H, m), 7.94 (1H, d, J=1.9 Hz), 8.04 (1H, d, J=9.0 Hz), 10.20 (1H, s).

Example 8

3-(3-Chloro-4-fluorophenoxy)-2-hydroxy-2-methyl-N-(3-methyl-4-nitrophenyl)propionamide 3-(3-Chloro-4-fluorophenoxy)-2-hydroxy-2-methyl-N-(3-methyl-4-nitrophenyl)propionamide was prepared as described in Example 1 starting from 3-chloro-4-fluorophenol and 1,2-epoxy-2-methyl-N-(3-methyl-4-nitrophenyl)-2-propanamide.

$^1$H NMR (400 MHz, DMSO-$d_6$): 1.42 (3H, s), 2.53 (3H, s), 4.00 (1H, d, J=9.8 Hz), 4.25 (1H, d, J=9.8 Hz), 6.21 (1H, s), 6.89-6.95 (1H, m), 7.15-7.19 (1 H, m), 7.26-7.32 (1H, m), 7.87 (1H, dd, J=8.9 Hz, J=2.3 Hz), 7.91 (1H, d, J=1.9 Hz), 8.03 (1H, d, J=8.9 Hz), 10.12 (1H, s).

Example 9

2-Hydroxy-2-methyl-N-(3-methyl-4-nitrophenyl)-3-(4-trifluoromethoxyphenoxy)propionamide 2-Hydroxy-2-methyl-N-(3-methyl-4-nitrophenyl)-3-(4-trifluoromethoxyphenoxy)propionamide was prepared as described in Example 1 starting from 4-(trifluoromethoxy)phenol and 1,2-epoxy-2-methyl-N-(3-methyl-4-nitrophenyl)-2-propanamide. $^1$H NMR (400 MHz, DMSO-$d_6$): 1.44 (3H, s), 2.53 (3H, s), 4.01 (1H, d, J=9.7 Hz), 4.24 (1H, d, J=9.7 Hz), 6.24 (1H, s), 6.99-7.05 (2H, m), 7.22-7.30 (2H, m), 7.88 (1H, dd, J=8.9 Hz, J=2.3 Hz), 7.93 (1H, d, J=1.9 Hz), 8.03 (1H, d, J=8.9 Hz), 10.14 (1H, s).

Example 10

3-(2,3-Dichlorophenoxy)-2-hydroxy-2-methyl-N-(3-methyl-4-nitrophenyl)propionamide 3-(2,3-Dichlorophenoxy)-2-hydroxy-2-methyl-N-(3-methyl-4-nitrophenyl)propionamide was prepared as described in Example 1 starting from 2,3-dichlorophenol and 1,2-epoxy-2-methyl-N-(3-methyl-4-nitrophenyl)-2-propanamide.

$^1$H NMR (400 MHz, DMSO-$d_6$): 1.46 (3H, s), 2.53 (3H, s), 4.16 (1H, d, J=9.8 Hz), 4.27 (1H, d, J=9.8 Hz), 6.27 (1H, s), 7.16-7.21(2H, m), 7.27-7.33 (1 H, m), 7.87 (1H, dd, J=8.9 Hz, J=2.3 Hz), 7.91 (1H, d, J=1.9 Hz), 8.03 (1H, d, J=8.9 Hz), 10.14 (1H, s)

Example 11

3-(4-Fluorophenoxy)-2-hydroxy-2-methyl-N-(3-methyl-4-nitrophenyl)propionamide 3-(4-Fluorophenoxy)-2-hydroxy-2-methyl-N-(3-methyl-4-nitrophenyl)propionamide was prepared as described in Example 1 starting from p-fluorophenol and 1,2-epoxy-2-methyl-N-[3-methyl-4-nitrophenyl]-2-propanamide. $^1$H NMR (400 MHz, DMSO-$d_6$): 1.43 (3H, s), 2.53 (3H, s), 3.96 (1H, d, J=9.6 Hz), 4.20 (1H, d, J=9.6 Hz), 6.21 (1H, s), 6.90-6.96 (2H, m), 7.06-7.12 (2H, m), 7.89 (1H, dd, J=9.0 Hz, J=2.2 Hz), 7.90 (1H, d, J=1.9 Hz), 8.04 (1H, d, J=9.0 Hz), 10.15 (1H, s).

Example 12

2-Hydroxy-2-methyl-N-(3-methyl-4-nitrophenyl)-3-p-tolyloxypropionamide

2-Hydroxy-2-methyl-N-(3-methyl-4-nitrophenyl)-3-p-tolyloxypropionamide was prepared as described in Example 1 starting from p-methylphenol and 1,2-epoxy-2-methyl-N-[3-methyl-4-nitrophenyl]-2-propanamide. $^1$H NMR (400 MHz, DMSO-$d_6$): 1.43 (3H, s), 2.21 (3H, s), 2.53 (3H, s), 3.93 (1H, d, J=9.6 Hz), 4.17 (1H, d, J=9.5 Hz), 6.18 (1H, s), 8.53 (2H, d, j=8.5 Hz), 7.06 (2H, d, j=8.4 Hz), 7.89 (1H, dd, J=2.2 Hz, J=9.0 Hz), 7.94 (1H, d, J=1.8 Hz), 8.04 (1H, d, J=9.0 Hz), 10.14 (1H, s).

Example 13

2-Hydroxy-2-methyl-N-(3-methyl-4-nitrophenyl)-3-[4-(2,2,2-trifluoroacetylamino)phenoxy]propionamide 2-Hydroxy-2-methyl-N-(3-methyl-4-nitrophenyl)-3-[4-(2,2,2-trifluoroacetylamino)phenoxy]propionamide was prepared as described in Example 1 starting from p-N-trifluoroacetamidophenol and 1,2-epoxy-2-methyl-N-[3-methyl-4-nitrophenyl]-2-propanamide. $^1$H NMR (400 MHz, DMSO-$d_6$): 1.43 (3H, s), 2.53 (3H, s), 3.98 (1H, d, J=9.6 Hz), 4.22 (1H, d, J=9.6 Hz), 6.22 (1H, s), 6.93-6.98 (2H, m), 7.52-7.56 (2H, m), 7.88 (1H, dd, J=9.0 Hz, J=2.2 Hz), 7.93 (1H, d, J=1.9 Hz), 8.04 (1H, d, J=9.0 Hz).

Example 14

2-Hydroxy-2-methyl-N-(3-methyl-4-nitrophenyl)-3-phenoxypropionamide

2-Hydroxy-2-methyl-N-(3-methyl-4-nitrophenyl)-3-phenoxypropionamide was prepared as described in Example 1 starting from phenol and 1,2-epoxy-2-methyl-N-[3-methyl-4-nitrophenyl]-2-propanamide. $^1$H NMR (400 MHz, DMSO-$d_6$): 1.44 (3H, s), 2.53 (3H, s), 3.97 (1H, d, J=9.6 Hz), 4.21 (1H, d, J=9.6 Hz), 6.21 (1H, s), 6.90-6.95 (3H, m), 7.24-7.29 (2H, m), 7.89 (1H, dd, J=2.3 Hz, J=9.0 Hz), 7.94 (1H, d, J=2.0 Hz), 8.04 (1H, d, $^3$J=9.0 Hz), 10.16 (1H, s).

Example 15

2-Hydroxy-2-methyl-N-(3-methyl-4-nitrophenyl)-3-(4-trifluoromethylphenoxy)propionamide 2-Hydroxy-2-methyl-N-(3-methyl-4-nitrophenyl)-3-(4-trifluoromethylphenoxy)propionamide was prepared as described in Example 1 starting from p-hydroxybenzotrifluoride and 2-methyloxirane-2-carbocylic acid (3-methyl-4-nitrophenyl)amide. The crude product was purified by flash chromatography using heptane/ethyl acetate (95:5) as eluent. Crystallization from toluene. $^1$H NMR (400 MHz, CDCl$_3$): 1.62 (3H, s), 2.65 (3H, s), 3.25 (1H, s, —OH), 4.05 (1H, d, $^2$J$_{gem}$=9.1 Hz), 4.51 (1H, d, $^2$J$_{gem}$=9.0 Hz), 7.00 (2H, d, $^3$J=8.8 Hz), 7.57 (2H, d, $^3$J=8.8 Hz), 7.58 (1H, dd, $^3$J=8.9 Hz, $^4$J=2.7 Hz), 7.66 (1H, d, $^4$J=2.2 Hz), 8.08 (1H, d, $^3$J=8.9 Hz), 8.9 (1H, broad s, —NHCO—).

Example 16

3-(4-Acetylphenoxy)-2-hydroxy-2-methyl-N-(3-methyl-4-nitrophenyl)propionamide 3-(4-Acetylphenoxy)-2-hydroxy-2-methyl-N-(3-methyl-4-nitrophenyl)propionamide was prepared as described in Example 1 starting from 4'-hydroxy-acetophenone and 2-methyloxirane-2-carbocylic acid (3-methyl-4-nitrophenyl)amide. The crude product was purified by flash chromatography using heptane/ethyl acetate (95:5) as eluent. Crystallization from toluene, m.p. 153-155° C. $^1$H NMR (400 MHz, CDCl$_3$): 1.62 (3H, s), 2.57 (3H, s), 2.65 (3H, s), 3.26 (1H, s, —OH), 4.07 (1H, d, $^2J_{gem}$=9.1 Hz), 4.53 (1H, d, $^2J_{gem}$=9.1 Hz), 6.96 (2H, d, $^3J$=8.9 Hz), 7.58 (1H, dd, $^3J$=8.9 Hz, $^4J$=2.4 Hz), 7.66 (1H, d, $^4J$=2.3 Hz), 7.94 (2H, d, $^3J$=8.9 Hz), 8.09 (1H, d, $^3J$=9.0 Hz), 8.95 (1H, broad s, —NHCO—).

Example 17

3-(4-Cyanophenoxy)-2-hydroxy-2-methyl-N-(3-methyl-4-nitrophenyl)propionamide 3-(4-Cyanophenoxy)-2-hydroxy-2-methyl-N-(3-methyl-4-nitrophenyl)propionamide was prepared as described in Example 1 starting from 4-cyanophenol and 2-methyloxirane-2-carbocylic acid (3-methyl-4-nitrophenyl)amide. The crude product was purified by flash chromatography using heptane/ethyl acetate as a gradient eluent. Crystallization from toluene. $^1$H NMR (400 MHz, DMSO-d$_6$): 1.44 (3H, s), 2.53 (3H, s), 4.08 (1H, d, $^2J_{gem}$=9.8 Hz), 4.33 (1H, d, $^2J_{gem}$=9.9 Hz), about 6.3 (1H, broad s, —OH), 7.10 (2H, d, $^3J$=8.8 Hz), 7.75 (2H, d, $^3J$=8.8 Hz), 7.88 (1H, dd, $^3J$=9.0 Hz, $^4J$=2.3 Hz), 7.93 (1H, d, $^4J$=2.0 Hz), 8.04 (1H, d, $^3J$=9.0 Hz), about 10.2 (1H, broad s, —NHCO—).

Example 18

3-(3-Fluorophenoxy)-2-hydroxy-2-methyl-N-(3-methyl-4-nitrophenyl)propionamide 3-(3-Fluorophenoxy)-2-hydroxy-2-methyl-N-(3-methyl-4-nitrophenyl)propionamide was prepared as described in Example 1 starting from 3-fluorophenol and 2-methyloxirane-2-carbocylic acid (3-methyl-4-nitrophenyl)amide. The crude product was purified by flash chromatography using heptane/ethyl acetate as a gradient eluent. Crystallization from toluene/heptane, m.p. 83-86° C. $^1$H NMR (400 MHz, DMSO-d$_6$): 1.43 (3H, s), 2.53 (3H, s), 3.99 (1H, d, $^2J_{gem}$=9.7 Hz), 4.24 (1H, d, $^2J_{gem}$=9.7 Hz), 6.26 (1H, broad s, —OH), 6.73-7.78 (2H, m), 6.81 (1H, m), 7.28 (1H, m), 7.89 (1H, dd, $^3J$=9.0 Hz, $^4J$=2.3 Hz), 7.94 (1H, d, $^4J$=2.0 Hz), 8.04 (1H, d, $^3J$=8.9 Hz), 10.17 (1H, broad s, —NHCO—).

Example 19

3-(2-Fluorophenoxy)-2-hydroxy-2-methyl-N-(3-methyl-4-nitrophenyl)propionamide 3-(2-Fluorophenoxy)-2-hydroxy-2-methyl-N-(3-methyl-4-nitrophenyl)propionamide was prepared as described in Example 1 starting from 2-fluorophenol and 2-methyloxirane-2-carbocylic acid (3-methyl-4-nitrophenyl)amide. The crude product was purified by flash chromatography using heptane/ethyl acetate (90:10) as eluent. Crystallization from ethyl acetate/heptane, m.p. 94-96° C. $^1$H NMR (400 MHz, DMSO-d$_6$): 1.44 (3H, s), 2.53 (3H, s), 4.07 (1H, d, $^2J_{gem}$=9.8 Hz), 4.27 (1H, d, $^2J_{gem}$=9.8 Hz), 6.27 (1H, broad s, —OH), 6.93 (1H, m), 7.10 (1H, m), 7.14-7.21 (2H, m), 7.88 (1H, dd, $^3J$=9.0 Hz, $^4J$=2.2 Hz), 7.93 (1H, d, $^4J$=2.0 Hz), 8.04 (1H, d, $^3J$=9.0 Hz), 10.17 (1H, broad s, —NHCO—)

Example 20

2-Hydroxy-3-[4-(2-hydroxyethyl)phenoxy]-2-methyl-N-(3-methyl-4-nitrophenyl)propionamide 2-Hydroxy-3-[4-(2-hydroxyethyl)phenoxy]-2-methyl-N-(3-methyl-4-nitrophenyl)propionamide was prepared as described in Example 1 starting from 4-hydroxyphenyl alcohol (1.45 eq.), sodium hydride (2.9 eq.) and 2-methyloxirane-2-carbocylic acid (3-methyl-4-nitrophenyl)amide (1 eq.). The crude product was purified by flash chromatography using heptane/ethyl acetate as a gradient eluent (9:1-4:6). $^1$H NMR (400 MHz, DMSO-d$_6$): 1.43 (3H, s), 2.53 (3H, s), 2.63 (2H, t, $^3J$=7.1 Hz), 3.53 (2H, m), 3.94 (1H, d, $^2J_{gem}$=9.6 Hz), 4.17 (1H, d, $^2J_{gem}$=9.6 Hz), 4.56 (1H, t, $^3J$=5.2 Hz, CH$_2$OH), 6.17 (1H, broad s, —OH), 6.81 (2H, d, $^3J$=8.7 Hz), 7.09 (2H, d), 7.88 (1H, dd, $^3J$=9.0 Hz, $^4J$=2.3 Hz), 7.93 (1H, d, $^4J$=1.9 Hz), 8.04 (1H, d, $^3J$=9.0 Hz), 10.13 (1H, broad s, —NHCO—).

Example 21

3-(2,6-Dichlorophenoxy)-2-hydroxy-2-methyl-N-(3-methyl-4-nitrophenyl)propionamide 3-(2,6-Dichlorophenoxy)-2-hydroxy-2-methyl-N-(3-methyl-4-nitrophenyl)propionamide was prepared as described Example 1 starting from 2,6-dichlorophenol and 1,2-epoxy-2-methyl-N-(3-methyl-4-nitrophenyl)-2-propanamide. $^1$H NMR (400 MHz, DMSO-d$_6$): 1.47 (3H, s), 2.53 (3H, s), 4.12 (1H, d, J=9.0 Hz), 4.18 (1H, d, J=9.0 Hz), 6.14 (1H, s), 7.12-7.18 (1H, m), 7.43-7.46 (2H, m), 7.86-7.90 (2H, m), 8.02-8.05 (1H, m), 10.11 (1H, s).

Example 22

3-(4-Bromo-2-fluorophenoxy)-2-hydroxy-2-methyl-N-(3-methyl-4-nitrophenyl)propionamide 3-(4-Bromo-2-fluorophenoxy)-2-hydroxy-2-methyl-N-(3-methyl-4-nitrophenyl)propionamide was prepared as described in Example 1 starting from 4-bromo-2-fluorophenol and 1,2-epoxy-2-methyl-N-(3-methyl-4-nitrophenyl)-2-propanamide. $^1$H NMR (400 MHz, DMSO-d$_6$): 1.43 (3H, s), 2.53 (3H, s), 4.08 (1H, d, J=9.9 Hz), 4.28 (1H, d, J=9.9 Hz), 6.26 (1H, s), 7.15-7.22 (1H, m), 7.29-7.33 (1 H, m), 7.46-7.50 (1H, m), 7.86 (1H, dd, J=8.9 Hz, J=2.3 Hz), 7.88 (1H, d, J=1.9 Hz), 8.03 (1H, J=8.9 Hz), 10.13 (1H, s).

Example 23

3-(4-Chlorophenoxy)-2-hydroxy-2-methyl-N-(3-methyl-4-nitrophenyl)propionamide 3-(4-Chlorophenoxy)-2-hydroxy-2-methyl-N-(3-methyl-4-nitrophenyl)propionamide was prepared as described in Example 1 starting from p-chlorophenol and 1,2-epoxy-2-methyl-N-[3-methyl-4-nitrophenyl]-2-propanamide. $^1$H NMR (400 MHz, DMSO-d$_6$): 1.43 (3H, s), 2.53 (3H, s), 3.98 (1H, d, J=9.7 Hz), 4.22 (1H, d, J=9.7 Hz), 6.23 (1H, s), 6.93-7.00 (2H, m), 7.28-7.32 (2H, m), 7.88 (1H, dd, J=9.0 Hz, J=2.2 Hz), 7.93 (1H, d, J=1.9 Hz), 8.04 (1H, d, J=9.0 Hz), 10.51 (1H, s).

Example 24

3-(4-Bromophenoxy)-2-hydroxy-2-methyl-N-(3-methyl-4-nitrophenyl)propionamide 3-(4-Bromophenoxy)-2-hydroxy-2-methyl-N-(3-methyl-4-nitrophenyl)propionamide was prepared as described in Example 1 starting from p-bromophenol and 1,2-epoxy-2-methyl-N-[3-methyl-4-nitrophenyl]-2-propanamide. $^1$H NMR (400 MHz, DMSO-$d_6$): 1.43 (3H, s), 2.53 (3H, s), 3.97 (1H, d, J=9.7 Hz), 4.21 (1H, d, J=9.7 Hz), 6.23 (1H, s), 6.88-6.93 (2H, m), 7.39-7.44 (2H, m), 7.88 (1H, dd, J=9.0 Hz, J=2.2 Hz), 7.93 (1H, d, J=1.8 Hz), 8.04 (1H, d, J=9.0 Hz), 10.15 (1H, s).

Example 25

2-Hydroxy-3-(4-methoxyphenoxy)-2-methyl-N-(3-methyl-4-nitrophenyl)propionamide 2-Hydroxy-3-(4-methoxyphenoxy)-2-methyl-N-(3-methyl-4-nitrophenyl)propionamide was prepared as described in Example 1 starting from p-methoxy-phenol and 1,2-epoxy-2-methyl-N-[3-methyl-4-nitrophenyl]-2-propanamide. $^1$H NMR (400 MHz, DMSO-$d_6$): 1.42 (3H, s), 2.53 (3H, s), 3.68 (3H, s), 3.91 (1H, d, J=9.5 Hz), 4.15 (1H, d, J=9.5 Hz), 6.17 (1H, s), 6.80-6.87 (4H, m), 7.88 (1H, dd, J=9.0 Hz, J=2.2 Hz), 7.93 (1H, d, J=2.0 Hz), 8.04 (1H, d, J=9.0 Hz), 10.13 (1H, s).

Example 26

3-(Benzo[1,3]dioxol-5-yloxy)-2-hydroxy-2-methyl-N-(3-methyl-4-nitrophenyl)propionamide 3-(Benzo[1,3]dioxol-5-yloxy)-2-hydroxy-2-methyl-N-(3-methyl-4-nitrophenyl)propionamide was prepared as described in Example 1 starting from 3,4-methylenedioxylphenol and 1,2-epoxy-2-methyl-N-[3-methyl-4-nitrophenyl]-2-propanamide. $^1$H NMR (400 MHz, DMSO-$d_6$): 1.41 (3H, s), 2.53 (3H, s), 3.90 (1H, d, J=9.6 Hz), 4.15 (1H, d, J=9.6 Hz), 5.94 (2H, s), 6.18 (1H, s), 6.35 (1H, dd, J=8.5 Hz, J=2.5 Hz), 6.59 (1H, d, J=2.5 Hz), 6.78 (1H, d, J=8.5 Hz), 7.88 (1H, dd, J=9.0 Hz, J=2.2 Hz), 7.93 (1H, d, J=1.6 Hz), 8.04 (1H, d, J=9.0 Hz), 10.13 (1H, s).

Example 27

3-(3,4-Dimethoxyphenoxy)-2-hydroxy-2-methyl-N-(3-methyl-4-nitrophenyl)propionamide 3-(3,4-Dimethoxyphenoxy)-2-hydroxy-2-methyl-N-(3-methyl-4-nitrophenyl)propionamide was prepared as described in Example 1 starting from 3,4-dimethoxy-phenol and 1,2-epoxy-2-methyl-N-[3-methyl-4-nitrophenyl]-2-propanamide. $^1$H NMR (400 MHz, DMSO-$d_6$): 1.43 (3H, s), 2.53 (3H, s), 3.67 (3H, s), 3.70 (3H, s), 3.91 (1H, d, J=9.6 Hz), 4.17 (1H, d, J=9.6 Hz), 6.17 (1H, s), 6.42 (1H, dd, J=8.8 Hz, J=2.8 Hz), 6.52 (1H, d, J=2.8 Hz), 6.82 (1H, d, J=8.8 Hz), 7.89 (1H, dd, J=9.0 Hz, J=2.2 Hz), 7.94 (1H, d, J=1.9 Hz), 8.04 (1H, d, J=9.0 Hz), 10.13 (1H, s).

Example 28

3-(3,4-Difluorophenoxy)-2-hydroxy-2-methyl-N-(3-methyl-4-nitrophenyl)propionamide 3-(3,4-Difluorophenoxy)-2-hydroxy-2-methyl-N-(3-methyl-4-nitrophenyl)propionamide was prepared as described in Example 1 starting from 3,4-difluorophenol and 1,2-epoxy-2-methyl-N-[3-methyl-4-nitrophenyl]-2-propanamide. $^1$H NMR (400 MHz, DMSO-$d_6$): 1.43 (3H, s), 2.53 (3H, s), 3.97 (1H, d, J=9.8 Hz), 4.23 (1H, d, J=9.8 Hz), 6.24 (1H, s), 6.72-6.79 (1H, m), 7.02-7.10 (1H, m), 7.20-7.33 (1H, m), 7.88 (1H, dd, J=9.0 Hz, J=2.2 Hz), 7.93 (1H, d, J=1.9 Hz), 8.04 (1H, d, J=9.9 Hz), 10.15 (1H, s).

Example 29

3-(2,4-Dichloro-3,5-dimethylphenoxy)-2-hydroxy-2-methyl-N-(3-methyl-4-nitrophenyl)propionamide 3-(2,4-Dichloro-3,5-dimethylphenoxy)-2-hydroxy-2-methyl-N-(3-methyl-4-nitrophenyl)-propionamide was prepared as described in Example 1 starting from 2,4-dichloro-3,5-dimethylphenol and 1,2-epoxy-2-methyl-N-[3-methyl-4-nitrophenyl]-2-propanamide. $^1$H NMR (400 MHz, DMSO-$d_6$): 1.46 (3H, s), 2.31 (3H, s), 2.36 (3H, s), 2.53 (3H, s), 4.41 (1H, d, J=9.7 Hz), 4.21 (1H, d, J=9.7 Hz), 6.25 (1H, s), 7.87 (1H, dd, J=9.0 Hz, J=2.3 Hz), 7.91 (1H, d, J=1.9 Hz), 8.04 (1H, d, J=9.0 Hz), 10.12 (1H, s).

Example 30

3-(6-Bromonaphtalen-2-yloxy)-2-hydroxy-2-methyl-N-(3-methyl-4-nitrophenyl)-propionamide 3-(6-Bromonaphtalen-2-yloxy)-2-hydroxy-2-methyl-N-(3-methyl-4-nitrophenyl)propionamide was prepared as described in Example 1 starting from 6-bromo-2-naphtol and 1,2-epoxy-2-methyl-N-[3-methyl-4-nitrophenyl]-2-propanamide. $^1$H NMR (400 MHz, DMSO-$d_6$): 1.49 (3H, s), 2.53 (3H, s), 4.11 (1H, d, J=9.7 Hz), 4.35 (1H, d, J=9.7 Hz), 6.29 (1H, s), 7.18 (1H, dd, J=9.0 Hz, J=2.5 Hz), 7.41 (1H, d, J=2.4 Hz), 7.57 (1H, dd, J=8.7 Hz, J=2.0 Hz), 7.77 (1H, d, J=9.1 Hz), 7.80 (1H, d, J=9.3 Hz), 7.90 (1H, dd, J=9.0 Hz, J=2.2 Hz), 7.95 (1H, d, 1.9 Hz), 8.05 (1H, d, J=9.0 Hz), 8.10 (1H, d, J=1.9 Hz), 10.21 (1H, s).

Example 31

3-(4-Acetylamino-3-trifluoromethylphenoxy)-2-hydroxy-2-methyl-N-(3-methyl-4-nitrophenyl)propionamide a) 4-Amino-3-trifluoromethylphenol

4-Nitro-3-trifluoromethylphenol (0.414 g; 2.0 mmol) was dissolved in 25 ml of glacial acetic acid and zinc dust (2.62 g; 40 mmol) was added in small portions during 10 minutes allowing the temperature to rise up to +40° C. The mixture was stirred for ten minutes and filtered. The dust was washed with 3×10 ml of glacial acetic acid and filtrate was evaporated to dryness to give 0.212 g of 4-amino-3-trifluoromethylphenol. $^1$H NMR (400 MHz, DMSO-$d_6$): 4.86 (2H, s), 6.72 (1H, d, J=8.7 Hz), 6.74 (1H, d, J=2.6 Hz), 6.78 (1H, dd, J=8.7 Hz, J=2.7 Hz), 8.91 (1H, s)

b) N-(4-Hydroxy-2-trifluoromethylphenyl)acetamide

4-Amino-3-trifluoromethylphenol (0.212 g; 1.2 mmol) was dissolved in 10 ml of glacial acetic acid under nitrogen atmosphere and acetic anhydride (0.3 ml; 3.0 mmol) was added followed with stirring for an hour at room temperature. Water (0.5 ml) was added into the reaction mixture and then evaporated to dryness. Toluene (50 ml) was added and the evaporation was repeated to give a quantitative yield of pure N-(4-Hydroxy-2-trifluoromethylphenyl)acetamide. $^1$H NMR (400 MHz, DMSO-$d_6$): 1.99 (3H, s), 7.01 (1H, dd, J=8.6 Hz, J=2.6 Hz), 7.02 (1H, d, J=2.5 Hz), 7.19 (1H, d, J=8.4 Hz), 9.33 (1H, s), 10.08 (1H, br s).

c) 3-(4-Acetylamino-3-trifluoromethylphenoxy)-2-hydroxy-2-methyl-N-(3-methyl-4-nitrophenyl)propionamide 3-(4-Acetylamino-3-trifluoromethylphenoxy)-2-hydroxy-2-methyl-N-(3-methyl-4-nitrophenyl)propionamide was prepared as described in Example 1 starting from N-(4-hydroxy-2-trifluoromethylphenyl)acetamide and 1,2-epoxy-2-methyl-N-[3-methyl-4-nitrophenyl]-2-propanamide. $^1$H NMR (400 MHz, DMSO-$d_6$): 1.46 (3H, s), 2.00 (3H, s), 2.53 (3H, s), 4.07 (1H, d, J=9.8 Hz), 4.32 (1H, d, J=9.8 Hz), 6.27 (1H, s), 7.19 (1H, d, J=2.7 Hz), 7.22 (1H, dd, J=9.0 Hz, J=2.5 Hz), 7.31 (1H, d, J=8.7 Hz), 7.88 (1H, dd, J=9.0 Hz, J=2.3 Hz), 7.93 (1H, d, J=2.0 Hz), 8.04 (1H, d, J=9.0 Hz), 9.43 (1H, s), 10.17 (1H, s).

Example 32

2-Hydroxy-2-methyl-N-(3-methyl-4-nitrophenyl)-3-(3,4,5-trifluorophenoxy)propionamide 2-Hydroxy-2-methyl-N-(3-methyl-4-nitrophenyl)-3-(3,4,5-trifluorophenoxy)propionamide was prepared as described in Example 1 starting from 3,4,5-trifluorophenol and 1,2-epoxy-2-methyl-N-[3-methyl-4-nitrophenyl]-2-propanamide. $^1$H NMR (400 MHz, DMSO-$d_6$): 1.42 (3H, s), 2.53 (3H, s), 3.98 (1H, d, J=9.9 Hz), 4.26 (1H, d, J=9.0 Hz), 6.27 (1H, s), 6.92-7.02 (2H, m), 7.88 (1H, dd, J=9.0 Hz, J=2.2 Hz), 7.92 (1H, d, J=1.9 Hz), 8.04 (1H, d, J=9.0 Hz), 10.14 (1H, s).

Example 33

2-Hydroxy-3-(1H-indol-5-yloxy)-2-methyl-N-(3-methyl-4-nitrophenyl)propionamide

2-Hydroxy-3-(1H-indol-5-yloxy)-2-methyl-N-(3-methyl-4-nitrophenyl)propionamide was prepared as described in Example 1 starting from 4-hydroxyindole and 1,2-epoxy-2-methyl-N-[3-methyl-4-nitrophenyl]-2-propanamide. $^1$H NMR (400 MHz, DMSO-$d_6$): 1.49 (3H, s), 2.53 (3H, s), 4.10 (1H, d, J=9.4 Hz), 4.23 (1H, d, J=9.4 Hz), 6.22 (1H, s), 6.31 (1H, d, J=2.2 Hz), 6.47 (1H, dd, J=6.8 Hz, J=1.5 Hz), 6.93-7.00 (2H, m), 7.12-7.17 (1H, m), 7.92 (1H, dd, J=9.0 Hz, J=2.1 Hz), 7.98 (1H, d, J=1.6 Hz), 8.05 (1H, d, J=9.0 Hz), 10.24 (1H, s), 11.02 (1H, s).

Example 34

2-Hydroxy-2-methyl-N-(3-methyl-4-nitrophenyl)-3-(4-methylsulfanyl-phenoxy)propionamide 2-Hydroxy-2-methyl-N-(3-methyl-4-nitrophenyl)-3-(4-methylsulfanyl-phenoxy)propionamide was prepared as described in Example 1 starting from 4-(methylthio)phenol and 1,2-epoxy-2-methyl-N-[3-methyl-4-nitrophenyl]-2-propanamide. $^1$H NMR (400 MHz, DMSO-$d_6$): 1.43 (3H, s), 2.41 (3H, s), 2.53 (3H, s), 3.96 (1H, d, J=9.6 Hz), 4.20 (1H, d, J=9.6 Hz), 6.21 (1H, s), 6.87-6.93 (2H, m), 7.17-7.25 (2H, m), 7.88 (1H, dd, J=9.0 Hz, J=2.3 Hz), 7.93 (1H, d, J=2.0 Hz), 8.04 (1H, d, J=9.0 Hz), 10.15 (1H, s).

Example 35

3-(3-Fluoro-4-nitrophenoxy)-2-hydroxy-2-methyl-N-(3-methyl-4-nitrophenyl)propionamide 3-(3-Fluoro-4-nitrophenoxy)-2-hydroxy-2-methyl-N-(3-methyl-4-nitrophenyl)propionamide was prepared as described in Example 1 starting from 3-fluoro-4-nitrophenol and 2-methyl-oxirane-2-carboxylic acid (3-methyl-4-nitrophenyl)amide. $^1$H NMR (DMSO-$d_6$): 1.46 (3H, s), 2.53 (3H, s), 4.16 (1H, d, J=10.1 Hz), 4.41 (1H, d, J=10.1 Hz), 6.36 (1H, bs), 6.96 (1H, m), 7.22 (1H, m), 7.88 (1H, dd, J=9.0 Hz and 2.1 Hz), 7.90 (1H, d, J=2.1 Hz), 8.04 (1H, d, J=9.0 Hz), 8.24 (1H, m), 10.19 (1H, s).

Example 36

3-[4-(4-Chlorobenzoyl)phenoxy]-2-hydroxy-2-methyl-N-(3-methyl-4-nitrophenyl)propionamide 3-[4-(4-Chlorobenzoyl)phenoxy]-2-hydroxy-2-methyl-N-(3-methyl-4-nitrophenyl)propionamide was prepared as described in Example 1 starting from 4-chloro-4'-hydroxybenzophenone and 2-methyloxirane-2-carbocylic acid (3-methyl-4-nitrophenyl)amide. The crude product was purified by flash chromatography using heptane/ethyl acetate as a gradient eluent. Crystallization from isopropanol.

$^1$H NMR (400 MHz, DMSO-$d_6$): 1.46 (3H, s), 2.53 (3H, s), 4.11 (1H, d, $^2J_{gem}$=9.7 Hz), 4.33 (1H, d, $^2J_{gem}$=9.7 Hz), about 6.3 (1H, broad s, —OH), 7.09 (2H, d, $^3J$=8.8 Hz), 7.62 (2H, d, $^3J$=8.5 Hz), 7.70 (2H, d, $^3J$=8.6 Hz) 7.72 (2H, d, $^3J$=9.0 Hz), 7.89 (1H, dd, $^3J$=9.0 Hz, $^4J$=2.3 Hz), 7.94 (1H, d, $^4J$=2.2 Hz), 8.05 (1H, d, $^3J$=9.0 Hz), about 10.2 (1H, broad s, —NHCO—).

Example 37

3-(3-Chlorophenoxy)-2-hydroxy-2-methyl-N-(3-methyl-4-nitrophenyl)propionamide 3-(3-Chlorophenoxy)-2-hydroxy-2-methyl-N-(3-methyl-4-nitrophenyl)propionamide was prepared as described in Example 1 starting from 3-chlorophenol and 2-methyloxirane-2-carbocylic acid (3-methyl-4-nitrophenyl)amide. The crude product was purified by flash chromatography using heptane/ethyl acetate as a gradient eluent (10:90-40:90). Crystallization from toluene, m.p. 104-107° C. $^1$H NMR (400 MHz, DMSO-$d_6$): 1.43 (3H, s), 2.53 (3H, s), 4.00 (1H, d, $^2J_{gem}$=9.8 Hz), 4.26 (1H, d, $^2J_{gem}$=9.8 Hz), 6.25 (1H, broad s, —OH), 6.88-6.91 (1H, m), 6.97-7.00 (1H, m), 7.02 (1H, t, $^4J$=2.1 Hz), 7.28 (1H, t, $^3J$=8.2 Hz), 7.89 (1H, dd, $^3J$=9.0 Hz, $^4J$=2.3 Hz), 7.94 (1H, d, $^4J$=2.2 Hz), 8.04 (1H, d, $^3J$=9.0 Hz), 10.17 (1H, broad s, —NHCO—).

Example 38

2-Hydroxy-2-methyl-N-(3-methyl-4-nitrophenyl)-3-pentafluorophenyloxy-propionamide 2-Hydroxy-2-methyl-N-(3-methyl-4-nitrophenyl)-3-pentafluorophenyloxy-propionamide was prepared as described in Example 1 starting from pentafluoro-phenol and 1,2-epoxy-2-methyl-N-[3-methyl-4-nitrophenyl]-2-propanamide. $^1$H NMR (400 MHz, DMSO-$d_6$): 1.40 (3H, s), 2.53 (3H, s), 4.24 (1H, d, J=10.2 Hz), 4.44 (1H, d, J=10.2 Hz), 6.28 (1H, s), 7.87 (1H, dd, J=9.0 Hz, J=2.1 Hz), 7.89 (1H, d, J=2.1 Hz), 8.05 (1H, d, J=8.9 Hz), 10.13 (1H, s).

Example 39

(2S)-3-(4-Fluorophenoxy)-2-hydroxy-2-methyl-N-(3-methyl-4-nitrophenyl)propionamide (2S)-3-(4-Fluorophenoxy)-2-hydroxy-2-methyl-N-(3-methyl-4-nitrophenyl)propionamide was prepared as described in Example 3 starting from p-fluorophenol and (2R)-3-Bromo-2-hydroxy-2-methylpropanoic acid. $^1$H NMR (400 MHz, DMSO-$d_6$): 1.43 (3H, s), 2.53 (3H, s), 3.95 (1H, d, J=9.6 Hz), 4.20 (1H, d, J=9.6 Hz), 6.21 (1H, s), 6.90-6.97 (2H, m), 7.06-7.12 (2H, m), 7.88 (1H, dd, J=9.0 Hz, J=2.3 Hz), 7.93 (1H, d, J=1.9 Hz), 8.04 (1H, d, J=9.0 Hz), 10.15 (1H, s).

Example 40

N-(4-Cyano-3-methylphenyl)-3-(4-fluorophenoxy)-2-hydroxy-2-methylpropionamide a) 4-Amino-2-methylbenzonitrile 3-Methyl-4-nitrobenzonitrile (1.0 g, 6 mmol) was dissolved in acetic acid (15 ml). Water (3.75 ml) was added and the mixture was heated between 90-95° C. Iron powder (2.5 g) was added during 1.5 hours and the resulting mixture was heated for 1 hour. Other portion of water (3.75 ml) was added and the heating was continued for additional 2 hours. The solution was allowed to cool to room temperature and the mixture was diluted with water (100 ml) and extracted with ethyl acetate (4×40 ml). The organic phase was washed with 5% NaHCO$_3$ (1×50 ml) and water (1×50 ml), dried over Na$_2$SO$_4$ and evaporated. The crude product was used without further purifications. $^1$H NMR (DMSO-$d_6$): 2.28 (3H, s), 6.04 (2H, bs), 6.44 (1H, m), 6.48 (1H, m), 7.31 (1H, m).

b) N-(4-Cyano-3-methylphenyl)-2-methylacrylamide

N-(4-Cyano-3-methylphenyl)-2-methylacrylamide was prepared as described in Example 1 starting from 4-amino-2-methylbenzonitrile and methacryloyl chloride.

$^1$H NMR (DMSO-$d_6$): 1.96 (3H, s), 2.45 (3H, s), 5.60 (1H, m), 5.85 (1H, m), 7.70 (2H, m), 7.81 (1H, m), 10.12 (1H, s).

c) 2-Methyloxirane-2-carboxylic acid (4-cyano-3-methylphenyl)amide

2-Methyloxirane-2-carboxylic acid (4-cyano-3-methylphenyl)amide was prepared as described in Example 1 starting from N-(4-cyano-3-methylphenyl)-2-methylacrylamide. $^1$H NMR (DMSO-$d_6$): 1.54 (3H, s), 2.43 (3H, s), 2.99 (1H, d, J=5.1 Hz), 3.04 (1H, d, J=5.1 Hz), 7.70 (2H, m), 7.89 (1H, m), 9.77 (1H, s).

d) N-(4-Cyano-3-methylphenyl)-3-(4-fluorophenoxy)-2-hydroxy-2-methylpropionamide N-(4-Cyano-3-methylphenyl)-3-(4-fluorophenoxy)-2-hydroxy-2-methylpropionamide was prepared as described in Example 1 starting from 4-fluorophenol and 2-methyl-oxirane-2-carboxylic acid (4-cyano-3-methylphenyl)amide. $^1$H NMR (DMSO-$d_6$): 1.42 (3H, s), 2.44 (3H, s), 3.94 (1H, d, J=9.6 Hz), 4.18 (1H, d, J=9.6 Hz), 6.18 (1H, bs), 6.93 (2H, m), 7.08 (2H, m), 7.69 (1H, d, J=9.0 Hz), 7.78 (1H, dd, J=9.0 Hz and 2.1 Hz), 7.93 (1H, d, J=2.1 Hz), 10.02 (1H, s).

Example 41

3-(4-Acetylamino-3-fluorophenoxy)-N-(4-cyano-3-methylphenyl)-2-hydroxy-2-methylpropionamide 3-(4-Acetylamino-3-fluorophenoxy)-N-(4-cyano-3-methylphenyl)-2-hydroxy-2-methylpropionamide was prepared as described in Example 1 starting from N-(2-fluoro-4-hydroxyphenyl)acetamide and 2-methyl-oxirane-2-carboxylic acid (4-cyano-3-methylphenyl)amide. $^1$H NMR (DMSO-$d_6$): 1.41 (3H, s), 2.02 (3H, s), 2.44 (3H, s), 3.95 (1H, d, J=9.8 Hz), 4.26 (1H, d, J=9.8 Hz), 6.21 (1H, bs), 6.72 (1H, m), 6.86 (1H, m), 7.56 (1H, m,) 7.69 (1H, d, J=9.0 Hz), 7.78 (1H, dd, J=9.0 Hz and 2.2 Hz), 7.93 (1H, d, J=2.2 Hz), 9.51 (1H, s), 9.99 (1H, bs).

Example 42

3-(4-Cyano-3-fluorophenoxy)-2-hydroxy-2-methyl-N-(3-methyl-4-nitrophenyl)propionamide 3-(4-Cyano-3-fluorophenoxy)-2-hydroxy-2-methyl-N-(3-methyl-4-nitrophenyl)propionamide was prepared as described in Example 1 starting from 2-fluoro-4-hydroxybenzonitrile and 2-methyl-oxirane-2-carboxylic acid (3-methyl-4-nitrophenyl)amide. $^1$H NMR (DMSO-$d_6$): 1.46 (3H, s), 2.53 (3H, s), 4.11 (1H, d, J=10.1 Hz), 4.371 (1H, d, J=10.1 Hz), 6.33 (1H, bs), 6.96 (1H, m), 7.18 (1H, m), 7.80 (1H, m), 7.88 (1H, dd, J=9.0 Hz and 2.1 Hz), 7.91 (1H, d, J=2.1 Hz), 8.03 (1H, d, J=9.0 Hz), 10.21 (1H, s).

Example 43

(2S)-3-(4-Cyano-3-fluorophenoxy)-2-hydroxy-2-methyl-N-(3-methyl-4-nitrophenyl)propionamide (2S)-3-(4-Cyano-3-fluorophenoxy)-2-hydroxy-2-methyl-N-(3-methyl-4-nitrophenyl)propionamide was prepared as described in Example 3 starting from 2-fluoro-4-hydroxybenzonitrile and (2R)-3-bromo-2-hydroxy-2-methyl-N-(3-methyl-4-nitrophenyl)propionamide according to the following procedure. A solution of 2-fluoro-4-hydroxybenzonitrile (0.2 g, 1.4 mmol), (2R)-3-bromo-2-hydroxy-2-methyl-N-(3-methyl-4-nitrophenyl)propionamide (0.37 g, 1.2 mmol), K$_2$CO$_3$ (0.34 g, 2.5 mmol) and benzyltriethylammonium chloride (0.028 g, 0.1 mmol) in methyl ethyl ketone (40 ml) was refluxed for 5 hours. The mixture was cooled to the room temperature and evaporated. The residue was partitioned between ethyl acetate (50 ml) and water (50 ml) and the phases were separated. The organic phase was washed with 1 M Na$_2$CO$_3$ (4×20 ml) and water (1×20 ml), dried over Na$_2$SO$_4$ and evaporated. The crude product was purified by flash chromatography (eluent CH$_2$Cl$_2$). $^1$H NMR (DMSO-$d_6$): 1.46 (3H, s), 2.53 (3H, s), 4.11 (1H, d, J=10.1 Hz), 4.371 (1H, d, J=10.1 Hz), 6.33 (1H, bs), 6.96 (1H, m), 7.18 (1H, m), 7.80 (1H, m), 7.88 (1H, dd, J=9.0 Hz and 2.1 Hz), 7.91 (1H, d, J=2.1 Hz), 8.03 (1H, d, J=9.0 Hz) 10.21 (1H, s).

Example 44

3-(4-Chloro-3-nitrophenoxy)-2-hydroxy-2-methyl-N-(3-methyl-4-nitrophenyl)propionamide 3-(4-Chloro-3-nitrophenoxy)-2-hydroxy-2-methyl-N-(3-methyl-4-nitrophenyl)propionamide was prepared as described in Example 1 starting from 4-chloro-3-nitrophenol and 2-methyloxirane-2-carboxylic acid (3-methyl-4-nitrophenyl)amide. The crude product was purified by flash chromatography (dichloromethane-0.2% methanol). $^1$H NMR (400 MHz, DMSO-$d_6$): 1.45 (3H, s), 2.53 (3H, s), 4.10 (1H, d, J=9.9 Hz), 4.36 (1H, d, J=9.9 Hz), 6.28 (1H, s), 7.28 (1H, dd, J=9.0 Hz, J=3.0 Hz), 7.62 (1H, d, J=9.0 Hz), 7.68 (1H, d, J=3.0 Hz), 7.88 (1H, dd, J=9.0 Hz, J=2.3 Hz), 7.92 (1H, d, J=2.0 Hz), 8.03 (1H, d, J=9.0 Hz), 10.15 (1H, s).

Example 45

3-(4-Fluoro-3-trifluoromethylphenoxy)-2-hydroxy-2-methyl-N-(3-methyl-4-nitrophenyl)propionamide 3-(4-Fluoro-3-trifluoromethylphenoxy)-2-hydroxy-2-methyl-N-(3-methyl-4-nitrophenyl)propionamide was prepared as described in Example 1 starting from 4-fluoro-3-(trifluoromethyl)phenol and 2-methyloxirane-2-carboxylic acid (3-methyl-4-nitrophenyl)amide. The crude product was purified by flash chromatography (dichloromethane-1% methanol). $^1$H NMR (400 MHz, DMSO-$d_6$): 1.44 (3H, s), 2.53 (3H, s), 4.06 (1H, d, J=9.9 Hz), 4.32 (1H, d, J=9.9 Hz), 6.23 (1H, s), 7.24-7.31 (2H, m), 7.38-7.43 (1H, m), 7.87 (1H, dd, J=9.0 Hz, J=2.1 Hz), 7.91 (1H, d, J=2.0 Hz), 8.03 (1H, d, J=9.0 Hz), 10.14 (1H, s).

Example 46

2-Hydroxy-3-[4-(2-methoxyethyl)phenoxy]-2-methyl-N-(3-methyl-4-nitrophenyl)propionamide 2-Hydroxy-3-[4-(2-methoxyethyl)phenoxy]-2-methyl-N-(3-methyl-4-nitrophenyl)propionamide was prepared as described in Example 1 starting from 4-methoxyethylphenol and 2-methyloxirane-2-carboxylic acid (3-methyl-4-nitrophenyl)amide. The crude product was purified by flash chromatography (dichloromethane-1% methanol). $^1$H NMR (400 MHz, DMSO-$d_6$): 1.43 (3H, s), 2.53 (3H, s), 2.71 (2H, t, J=6.8 Hz), 3.21 (3H, s), 3.45 (2H, t, J=6.8 Hz), 3.94 (1H, d, J=9.5 Hz), 4.17 (1H, d, J=9.5 Hz), 6.20 (1H, s), 6.82 (2H, d, J=7.8 Hz), 7.10 (2H, d, J=8.0 Hz), 7.89 (1H, d, J=9.0 Hz), 7.94 (1H, s), 8.03 (1H, d, J=8.8 Hz), 10.16 (1H, s).

Example 47

3-(4-Fluorophenoxy)-2-hydroxy-2-methyl-N-(2-methyl-3-nitrophenyl)propionamide a) 2-Methyl-N-(2-methyl-3-nitrophenyl)acrylamide 2-Methyl-N-(2-methyl-3-nitrophenyl)acrylamide was prepared as described in Example 1a starting from 2-methyl-3-nitroaniline and methacryloyl chloride. $^1$H NMR (400 MHz, DMSO-$d_6$): 1.97 (3H, s), 2.23 (3H, s), 5.56 (1H, s), 5.90 (1H, s), 7.40-7.46 (1H, m), 7.57-7.60 (1H, m), 7.74-7.77 (1H, m), 9.71 (1H, s).

b) 2-Methyloxirane-2-carboxylic acid (2-methyl-3-nitrophenyl)amide

2-Methyloxirane-2-carboxylic acid (2-methyl-3-nitrophenyl)amide was prepared as described in Example 1b starting from 2-methyl-N-(2-methyl-3-nitrophenyl)acrylamide. $^1$H NMR (400 MHz, DMSO-$d_6$): 1.54 (3H, s), 2.19 (3H, s), 2.99 (1H, d, J=5.1 Hz), 3.09 (1H, d, J=5.1 Hz), 7.40-7.45 (1H, m), 7.57-7.60 (1H, m), 7.74-7.77 (1H, m), 9.47 (1H, s).

c) 3-(4-Fluorophenoxy)-2-hydroxy-2-methyl-N-(2-methyl-3-nitrophenyl)propionamide 3-(4-Fluorophenoxy)-2-hydroxy-2-methyl-N-(2-methyl-3-nitrophenyl)propionamide was prepared as described in Example 1c starting from 4-fluorophenol and 2-methyloxirane-2-carboxylic acid (2-methyl-3-nitrophenyl)amide. The crude product was purified by flash chromatography (dichloromethane-1% methanol). $^1$H NMR (400 MHz, DMSO-$d_6$): 1.44 (3H, s), 2.28 (3H, s), 3.96 (1H, d, J=9.5 Hz), 4.17 (1H, d, J=9.5 Hz), 6.14 (1H, s), 6.93-6.97 (2H, m), 7.08-7.13 (2H, m), 7.41-7.45 (1H, m), 7.66-7.68 (1H, m), 7.72-7.75 (1H, m), 9.72 (1H, s).

Example 48

3-(3-Chloro-4-fluorophenoxy)-2-hydroxy-2-methyl-N-(2-methyl-3-nitrophenyl)propionamide 3-(3-Chloro-4-fluorophenoxy)-2-hydroxy-2-methyl-N-(2-methyl-3-nitrophenyl)propionamide was prepared as described in Example 1 starting from 3-chloro-4-fluorophenol and 2-methyloxirane-2-carboxylic acid (2-methyl-3-nitrophenyl)amide. The crude product was purified by flash chromatography (dichloromethane-1% methanol). $^1$H NMR (400 MHz, DMSO-$d_6$): 1.44 (3H, s), 2.27 (3H, s), 3.99 (1H, d, J=9.8 Hz), 4.23 (1H, d, J=9.8 Hz), 6.15 (1H, s), 6.92-6.97 (1H, m), 7.17-7.20 (1H, m), 7.29-7.35 (1H, m), 7.41-7.46 (1H, m), 7.66-7.69 (1H, m), 7.72-7.75 (1H, m), 9.72 (1H, s).

Example 49

2-Hydroxy-3-[4-(2-methoxyethyl)phenoxy]-2-methyl-N-(2-methyl-3-nitrophenyl)propionamide 2-Hydroxy-3-[4-(2-methoxyethyl)phenoxy]-2-methyl-N-(2-methyl-3-nitrophenyl)propionamide was prepared as described in Example 1 starting from 4-methoxyethylphenol and 2-methyloxirane-2-carboxylic acid (2-methyl-3-nitrophenyl)amide. The crude product was purified by flash chromatography (dichloromethane-2% methanol). $^1$H NMR (400 MHz, DMSO-$d_6$): 1.44 (3H, s), 2.28 (3H, s), 2.72 (2H, t, J=6.8 Hz), 3.22 (3H, s), 3.47 (2H, t, J=6.8 Hz), 3.94 (1H, d, J=9.4 Hz), 4.15 (1H, d, J=9.4 Hz), 6.11 (1H, s), 6.84 (2H, d, J=7.9 Hz), 7.12 (2H, d, J=7.9 Hz), 7.41-7.45 (1H, m), 7.65-7.68 (1H, m), 7.72-7.75 (1H, m), 9.71 (1H, s).

Example 50

{2-Fluoro-4-[2-hydroxy-2-(3-methyl-4-nitrophenylcarbamoyl)propoxy]-phenyl}carbamic acid ethyl ester a) (2-Fluoro-4-hydroxyphenyl)carbamic acid ethyl ester Ethyl chloroformate (0.37 ml, 3.9 mmol) was added to a stirring solution of 4-amino-3-fluorophenol (0.5 g, 3.9 mmol) in 2 ml of 10% NaOH. The reaction mixture was heated at 80°

C. for 30 min. After cooling, the solution was acidified with hydrochloric acid to give the product. $^1$H NMR (400 MHz, DMSO-d$_6$): 1.20 (3H, t, J=7.0 Hz), 4.06 (2H, q, J=7.0 Hz), 6.53-6.59 (2H, m), 7.16-7.21 (1H, m), 8.79 (1H, s), 9.72 (1H, s).

b) {2-Fluoro-4-[2-hydroxy-2-(3-methyl-nitrophenyl-carbamoyl)propoxy]-phenyl}carbamic acid ethyl ester {2-Fluoro-4-[2-hydroxy-2-(3-methyl-4-nitrophenylcarbamoyl)propoxy]-phenyl}carbamic acid ethyl ester was prepared as described in Example 1 starting from (2-fluoro-4-hydroxyphenyl)carbamic acid ethyl ester and 2-methyloxirane-2-carboxylic acid (3-methyl-4-nitrophenyl)amide. The crude product was purified by flash chromatography (dichloromethane-1.8% methanol). $^1$H NMR (400 MHz, DMSO-d$_6$): 1.20 (3H, t, J=7.0 Hz), 1.43 (3H, s), 2.53 (3H, s), 3.97 (1H, d, J=9.7 Hz), 4.07 (2H, q, J=7.0 Hz), 4.22 (1H, d, J=9.7 Hz), 6.21 (1H, s), 6.71-6.73 (1H, m), 6.83-6.87 (1H, m), 7.31-7.35 (1H, m), 7.86-8.05 (3H, m), 8.95 (1H, s), 10.12 (1H, s).

Example 51

3-(4-Cyano-3-fluorophenoxy)-2-hydroxy-N-(3-hydroxymethyl-4-nitrophenyl)-2-methylpropionamide a) (5-Amino-2-nitrophenyl)methanol To a solution of 5-amino-2-nitrobenzoic acid (3.0 g, 16.4 mmol) in 40 ml of tetrahydrofuran was added 50 ml of borane-tetrahydrofuran complex (1.0 M solution in THF). The mixture was heated under reflux for one hour. The usual workup afforded the product. $^1$H NMR (400 MHz, DMSO-d$_6$): 4.79 (2H, d, J=5.4 Hz), 5.37 (1H, t, J=5.4 Hz), 6.48 (1H, dd, J=9.0 Hz, J=2.5 Hz), 6.68 (2H, s), 6.99 (1H, d, J=2.5 Hz), 7.94 (1H, d, J=9.0 Hz).

b) N-(3-Hydroxymethyl-4-nitrophenyl)-2-methylacrylamide

N-(3-Hydroxymethyl-4-nitrophenyl)-2-methylacrylamide was prepared as described in Example 1a starting from (5-Amino-2-nitrophenyl)methanol and methacryloyl chloride. $^1$H NMR (400 MHz, DMSO-d$_6$): 1.97 (3H, s), 4.85 (2H, d, J=5.2 Hz), 5.56 (1H, t, J=5.2 Hz), 5.61 (1H, s), 5.90 (1H, s), 7.93 (1H, dd, J=9.0 Hz, J=2.1 Hz), 8.11 (1H, d, J=9.0 Hz), 8.20 (1H, d, J=2.1 Hz), 10.32 (1H, s).

c) 2-Methyloxirane-2-carboxylic acid (3-hydroxymethyl-4-nitrophenyl)amide

2-Methyloxirane-2-carboxylic acid (3-hydroxymethyl-4-nitrophenyl)amide was prepared as described in Example 1b starting from N-(3-hydroxymethyl-4-nitrophenyl)-2-methylacrylamide. $^1$H NMR (400 MHz, DMSO-d$_6$): 1.55 (3H, s), 2.98 (1H, d, J=5.1 Hz), 3.07 (1H, d, J=5.1 Hz), 4.82 (2H, d, J=5.3 Hz), 5.53 (1H, t, J=5.3 Hz), 7.84 (1H, dd, J=8.9 Hz, J=2.4 Hz), 8.08 (1H, d, J=8.9 Hz), 8.24 (1H, d, J=2.4 Hz), 9.99 (1H, s).

d) 3-(4-Cyano-3-fluorophenoxy)-2-hydroxy-N-(3-hydroxymethyl-4-nitrophenyl)-2-methylpropionamide 3-(4-Cyano-3-fluorophenoxy)-2-hydroxy-N-(3-hydroxymethyl-4-nitrophenyl)-2-methylpropionamide was prepared as described in Example 1c starting from 2-fluoro-4-hydroxybenzonitrile and 2-methyloxirane-2-carboxylic acid (3-hydroxy-methyl-4-nitrophenyl)amide. The crude product was purified by flash chromatography (dichloromethane-6.6% methanol). $^1$H NMR (400 MHz, DMSO-d$_6$): 1.45 (3H, s), 4.13 (1H, d, J=10.0 Hz), 4.38 (1H, d, J=10.0 Hz), 4.83 (2H, d, J=5.4 Hz), 5.51 (1H, t, J=5.4 Hz), 6.25 (1H, s), 6.94-6.98 (1H, m), 7.16-7.20 (1H, m), 7.77-7.82 (1H, m), 7.88 (1H, dd, J=9.0 Hz, J=2.4 Hz), 8.09 (1H, d, J=9.0 Hz), 8.34 (1H, d, J=2.4 Hz), 10.24 (1H, s).

Example 52

3-(4-Fluorophenylamino)-2-hydroxy-2-methyl-N-(3-methyl-4-nitrophenyl)propionamide A mixture of 2-methyloxirane-2-carboxylic acid (3-methyl-4-nitrophenyl)amide (0.2 g, 0.85 mmol), 4-fluoroaniline (0.18 g, 1.7 mmol) and sodium perchlorate (0.21 g, 1.7 mmol) in 2 ml of acetonitrile was boiled under reflux for 6 hours. After a workup of the reaction mixture, the crude product was purified by flash chromatography (dichloromethane-1% methanol). $^1$H NMR (400 MHz, DMSO-d$_6$): 1.41 (3H, s), 2.51 (3H, s), 3.10 (1H, dd, J=12.7 Hz, J=4.6 Hz), 3.41 (1H, dd, J=12.7 Hz, J=7.7 Hz), 5.26 (1H, m), 6.02 (1H, s), 6.62-6.66 (2H, m), 6.84-6.89 (2H, m), 7.79-7.83 (2H, m), 8.02 (1H, d, J=8.9 Hz), 9.99 (1H, s).

Example 53

2-Hydroxy-2-methyl-N-(3-methyl-4-nitrophenyl)-3-(4-trifluoromethylphenylamino)propionamide 2-Hydroxy-2-methyl-N-(3-methyl-4-nitrophenyl)-3-(4-trifluoromethylphenylamino)propionamide was prepared as described in Example 52 starting from 4-(trifluoromethyl)aniline and 2-methyloxirane-2-carboxylic acid (3-methyl-4-nitrophenyl)amide. The crude product was purified by flash chromatography (dichloromethane-1.5% methanol). $^1$H NMR (400 MHz, DMSO-d$_6$): 1.42 (3H, s), 2.51 (3H, s), 3.23 (1H, dd, J=13.3 Hz, J=5.0 Hz), 3.51 (1H, dd, J=13.3 Hz, J=7.0 Hz), 6.06 (1H, s), 6.18 (1H, m), 6.77 (2H, d, J=8.4 Hz)), 7.31 (2H, d, J=8.4 Hz), 7.79-7.83 (2H, m), 8.01 (1H, d, J=8.9 Hz), 10.02 (1H, s).

Example 54

2-Hydroxy-3-(4-methoxy-3-trifluoromethylphenylamino)-2-methyl-N-(3-methyl-4-nitrophenyl)propionamide 2-Hydroxy-3-(4-methoxy-3-trifluoromethylphenylamino)-2-methyl-N-(3-methyl-4-nitrophenyl)propionamide was prepared as described in Example 52 starting from 3-amino-6-methoxybenzotrifluoride and 2-methyloxirane-2-carboxylic acid (3-methyl-4-nitrophenyl)amide. The crude product was purified by flash chromatography (dichloromethane-1.5% methanol). $^1$H NMR (400 MHz, DMSO-d$_6$): 1.41 (3H, s), 2.51 (3H, s), 3.12 (1H, dd, J=13.0 Hz, J=4.8 Hz), 3.45 (1H, dd, J=13.0 Hz, J=7.7 Hz), 3.71 (3H, s), 5.42 (1H, m), 6.00 (1H, s), 6.88 (1H, dd, J=8.9 Hz, J=2.7 Hz), 6.92 (1H, d, J=2.7 Hz), 6.97 (1H, d, J=8.9 Hz), 7.78 (1H, dd, J=8.9 Hz, J=2.3 Hz), 7.81 (1H, d, J=1.9 Hz), 8.00 (1H, d, J=8.9 Hz), 9.98 (1H, s).

Example 55

3-(4-Cyanophenylamino)-2-hydroxy-2-methyl-N-(3-methyl-4-nitrophenyl)propionamide 3-(4-Cyanophenylamino)-2-hydroxy-2-methyl-N-(3-methyl-4-nitrophenyl)propionamide was prepared as described in Example 52 starting from 4-aminobenzonitrile and 2-methyloxirane-2-carboxylic acid (3-methyl-4-nitrophenyl)amide. The crude product was purified by flash chromatography (dichloromethane-5% methanol). $^1$H NMR (400 MHz, DMSO-$d_6$): 1.41 (3H, s), 2.52 (3H, s), 3.25 (1H, dd, J=13.5 Hz, J=5.3 Hz), 3.52 (1H, dd, J=13.5 Hz, J=7.0 Hz), 6.08 (1H, s), 6.53 (1H, m), 6.75 (2H, d, J=8.8 Hz)), 7.39 (2H, d, J=8.8 Hz), 7.79-7.83 (2H, m), 8.01 (1H, d, J=8.9 Hz), 10.02 (1H, s).

Example 56

3-(3-Chloro-4-cyanophenylamino)-2-hydroxy-2-methyl-N-(3-methyl-4-nitrophenyl)propionamide 3-(3-Chloro-4-cyanophenylamino)-2-hydroxy-2-methyl-N-(3-methyl-4-nitrophenyl)propionamide was prepared as described in Example 52 starting from 4-amino-2-chlorobenzonitrile and 2-methyloxirane-2-carboxylic acid (3-methyl-4-nitrophenyl)amide. The crude product was purified by flash chromatography (dichloromethane-3% methanol). $^1$H NMR (400 MHz, DMSO-$d_6$): 1.40 (3H, s), 2.52 (3H, s), 3.27 (1H, dd, J=13.8 Hz, J=5.5 Hz), 3.55 (1H, dd, J=13.8 Hz, J=6.9 Hz), 6.12 (1H, s), 6.72 (1H, dd, J=8.8 Hz, J=2.2 Hz), 6.90 (1H, d, J=2.2 Hz), 6.95-6.98 (1H, m), 7.46 (1H, d, J=8.7 Hz), 7.80 (1H, dd, J=8.9 Hz, J=2.3 Hz), 7.83 (1H, d, J=2.0 Hz), 8.02 (1H, d, J=8.9 Hz), 10.05 (1H, s).

Example 57

2-Hydroxy-2-methyl-N-(3-methyl-4-nitrophenyl)-3-(pyridin-3-yloxo)propionamide

2-Hydroxy-2-methyl-N-(3-methyl-4-nitrophenyl)-3-(pyridin-3-yloxo)propionamide was prepared as described in Example 1 starting from 3-hydroxypyridine and 2-methyloxirane-2-carboxylic acid (3-methyl-4-nitrophenyl)amide. The crude product was purified by flash chromatography (dichloromethane-9% methanol). $^1$H NMR (400 MHz, DMSO-$d_6$): 1.45 (3H, s), 2.53 (3H, s), 4.06 (1H, d, J=9.8 Hz), 4.31 (1H, d, J=9.8 Hz), 6.26 (1H, s), 7.28-7.32 (1H, m), 7.38-7.41 (1H, m), 7.87-7.93 (2H, m), 8.03 (1H, d, J=8.9 Hz), 8.15-8.17 (1H, m), 8.26 (1H, d, J=2.4 Hz), 10.15 (1H, s).

Example 58

2-Hydroxy-2-methyl-N-(3-methyl-4-nitrophenyl)-3-(pyridin-4-yloxo)propionamide

2-Hydroxy-2-methyl-N-(3-methyl-4-nitrophenyl)-3-(pyridin-4-yloxo)propionamide was prepared as described in Example 1 starting from 4-hydroxypyridine and 2-methyloxirane-2-carboxylic acid (3-methyl-4-nitrophenyl)amide. The crude product was purified by flash chromatography (dichloromethane-7% methanol).

$^1$H NMR (400 MHz, CDCl$_3$): 1.62 (3H, s), 2.63 (3H, s), 4.08 (1H, d, J=9.2 Hz), 4.46 (1H, d, J=9.2 Hz), 6.79 (2H, d, J=5.1 Hz), 7.57 (1H, d, J=9.0 Hz), 7.66 (1H, s), 8.05 (1H, d, J=8.8 Hz), 8.35 (2H, d, J=5.1 Hz), 9.14 (1H, s).

Example 59

2-Hydroxy-2-methyl-N-(3-methyl-4-nitrophenyl)-3-(pyridin-2-yloxo)propionamide

2-Hydroxy-2-methyl-N-(3-methyl-4-nitrophenyl)-3-(pyridin-2-yloxo)propionamide was prepared as described in Example 1 starting from 2-hydroxypyridine and 2-methyloxirane-2-carboxylic acid (3-methyl-4-nitrophenyl)amide. The crude product was purified by flash chromatography (dichloromethane-2% methanol).

$^1$H NMR (400 MHz, CDCl$_3$): 1.53 (3H, s), 2.61 (3H, s), 4.58 (1H, d, J=12.3 Hz), 4.72 (1H, d, J=12.3 Hz), 6.87 (1H, d, J=8.3 Hz), 7.00 (1H, t, J=6.1 Hz), 7.56 (1H, d, J=8.9 Hz), 7.64-7.69 (2H, m), 7.81 (1H, s), 8.03 (1H, d, J=8.9 Hz), 8.11 (1H, d, J=5.0 Hz), 9.33 (1H, s).

Example 60

3-(2-Chloropyridin-3-yloxo)-2-hydroxy-2-methyl-N-(3-methyl-4-nitrophenyl)propionamide 3-(2-Chloropyridin-3-yloxo)-2-hydroxy-2-methyl-N-(3-methyl-4-nitrophenyl)propionamide was prepared as described in Example 1 starting from 2-chloro-3-hydroxypyridine and 2-methyloxirane-2-carboxylic acid (3-methyl-4-nitrophenyl)amide. The crude product was purified by flash chromatography (dichloromethane-2% methanol). $^1$H NMR (400 MHz, DMSO-$d_6$): 1.47 (3H, s), 2.53 (3H, s), 4.18 (1H, d, J=9.9 Hz), 4.31 (1H, d, J=9.9 Hz), 6.28 (1H, s), 7.35-7.39 (1H, m), 7.63 (1H, d, J=8.2 Hz), 7.77-7.97 (3H, m), 8.04 (1H, d, J=8.9 Hz), 10.13 (1H, s).

Example 61

N-(4-Fluoro-3-methylphenyl)-3-(4-fluorophenoxy)-2-hydroxy-2-methylpropionamide a) N-(4-Fluoro-3-methylphenyl)-2-methylacrylamide N-(4-Fluoro-3-methylphenyl)-2-methylacrylamide was prepared as described in Example 1a starting from 4-fluoro-3-methylaniline and methacryloyl chloride. $^1$H NMR (400 MHz, DMSO-$d_6$): 1.94 (3H, s), 2.21 (3H, s), 5.50 (1H, s), 5.78 (1H, s), 7.05-7.10 (1H, m), 7.48-7.51 (1H, m), 7.57-7.59 (1H, m), 9.75 (1H, s).

b) 2-Methyloxirane-2-carboxylic acid (4-fluoro-3-methylphenyl)amide

2-Methyloxirane-2-carboxylic acid (4-fluoro-3-methylphenyl)amide was prepared as described in Example 1b starting from N-(4-fluoro-3-methylphenyl)-2-methylacrylamide. $^1$H NMR (400 MHz, DMSO-$d_6$): 1.52 (3H, s), 2.19 (3H, s), 2.94 (1H, d, J=5.3 Hz), 2.99 (1H, d, J=5.3 Hz), 7.02-7.07 (1H, m), 7.44-7.48 (1H, m), 7.56-7.59 (1H, m), 9.40 (1H, s).

c) N-(4-Fluoro-3-methylphenyl)-3-(4-fluorophenoxy)-2-hydroxy-2-methylpropionamide N-(4-Fluoro-3-methylphenyl)-3-(4-fluorophenoxy)-2-hydroxy-2-methylpropionamide was prepared as described in Example 1c starting from 4-fluorophenol and 2-methyloxirane-2-carboxylic acid (4-fluoro-3-methylphenyl)amide. The crude product was purified by flash chromatography (dichloromethane-1.4% methanol).

$^1$H NMR (400 MHz, DMSO-$d_6$): 1.40 (3H, s), 2.20 (3H, s), 3.92 (1H, d, J=9.5 Hz), 4.17 (1H, d, J=9.5 Hz), 6.03 (1H, s), 6.91-6.95 (2H, m), 7.03-7.10 (3H, m), 7.53-7.57 (1H, m), 7.66-7.68 (1H, m), 9.62 (1H, s).

Example 62

3-(4-Acetylaminophenoxy)-N-(4-fluoro-3-methylphenyl)-2-hydroxy-2-methylpropionamide 3-(4-Acetylaminophenoxy)-N-(4-fluoro-3-methylphenyl)-2-hydroxy-2-methylpropionamide was prepared as described in Example 61 c starting from 4-acetamidophenol and 2-methyloxirane-2-carboxylic acid (4-fluoro-3-methylphenyl)amide. $^1$H NMR (400 MHz, DMSO-$d_6$): 1.40 (3H, s), 2.00 (3H, s), 2.20 (3H, s), 3.90 (1H, d, J=9.5 Hz), 4.15 (1H, d, J=9.5 Hz), 6.03 (1H, s), 6.84 (2H, d, J=8.7 Hz), 7.03-7.08 (1H, m), 7.44 (2H, d, J=8.7 Hz), 7.54-7.57 (1H, m), 7.67-7.69 (1H, m), 9.62 (1H, s), 9.75 (1H, s).

Example 63

3-(3-Chloro-4-cyanophenoxy)-2-hydroxy-2-methyl-N-(3-methyl-4-nitrophenyl)propionamide 3-(3-Chloro-4-cyanophenoxy)-2-hydroxy-2-methyl-N-(3-methyl-4-nitrophenyl)propionamide was prepared as described in Example 1 starting from 2-chloro-4-hydroxybenzonitrile and 2-methyloxirane-2-carboxylic acid (2-methyl-3-nitrophenyl)amide. The crude product was purified by flash chromatography (dichloromethane-1.2% methanol). $^1$H NMR (400 MHz, DMSO-$d_6$): 1.44 (3H, s), 2.53 (3H, s), 4.13 (1H, d, J=10.1 Hz), 4.39 (1H, d, J=10.1 Hz), 6.29 (1H, s), 7.09 (1H, dd, J=8.8 Hz, J=2.4 Hz), 7.36 (1H, d, J=2.4 Hz), 7.84-7.91 (3H, m), 8.03 (1H, d, J=8.9 Hz), 10.15 (1H, s).

Example 64

3-(4-Cyano-3-fluorophenoxy)-2-hydroxy-2-methyl-N-(2-methyl-4-nitrophenyl)propionamide a) 2-Methyl-N-(2-methyl-4-nitrophenyl)acrylamide 2-Methyl-N-(2-methyl-4-nitrophenyl)acrylamide was prepared as described in Example 1a starting from 2-methyl-4-nitroaniline and methacryloyl chloride. $^1$H NMR (400 MHz, DMSO-$d_6$): 1.98 (3H, s), 2.34 (3H, s), 5.59 (1H, s), 5.91 (1H, s), 7.74 (1H, d, J=8.8 Hz), 8.07 (1H, dd, J=8.8 Hz, J=2.7 Hz), 8.15 (1H, d, J=2.6 Hz), 9.53 (1H, s).

b) 2-Methyloxirane-2-carboxylic acid (2-methyl-4-nitrophenyl)amide

2-Methyloxirane-2-carboxylic acid (2-methyl-4-nitrophenyl)amide was prepared as described in Example 1b starting from 2-methyl-N-(2-methyl-4-nitrophenyl)acrylamide. $^1$H NMR (400 MHz, DMSO-$d_6$): 1.55 (3H, s), 2.30 (3H, s), 3.03 (1H, d, J=5.1 Hz), 3.15 (1H, d, J=5.1 Hz), 7.86 (1H, d, J=8.9 Hz), 8.08 (1H, dd, J=8.9 Hz, J=2.6 Hz), 8.15 (1H, d, J=2.5 Hz), 9.13 (1H, s).

c) 3-(4-Cyano-3-fluorophenoxy)-2-hydroxy-2-methyl-N-(2-methyl-4-nitrophenyl)propionamide 3-(4-Cyano-3-fluorophenoxy)-2-hydroxy-2-methyl-N-(2-methyl-4-nitrophenyl)propionamide was prepared as described in Example 1c starting from 2-fluoro-4-hydroxybenzonitrile and 2-methyloxirane-2-carboxylic acid (2-methyl-4-nitrophenyl)amide. The crude product was purified by flash chromatography (dichloromethane-1.3% methanol). $^1$H NMR (400 MHz, DMSO-$d_6$): 1.46 (3H, s), 2.37 (3H, s), 4.13 (1H, d, J=10.1 Hz), 4.37 (1H, d, J=10.1 Hz), 6.51 (1H, s), 6.95-6.98 (1H, m), 7.17-7.21 (1H, m), 7.78-7.83 (1H, m), 8.05-8.12 (2H, m), 8.18 (1H, d, J=2.3 Hz), 9.57 (1H, s).

Example 65

3-(3-chloro-4-cyanophenoxy)-2-hydroxy-2-methyl-N-(2-methyl-4-nitrophenyl)propionamide 3-(3-Chloro-4-cyanophenoxy)-2-hydroxy-2-methyl-N-(2-methyl-4-nitrophenyl)propionamide was prepared as described in Example 64c starting from 2-chloro-4-hydroxybenzonitrile and 2-methyloxirane-2-carboxylic acid (2-methyl-4-nitrophenyl)amide. The crude product was purified by flash chromatography (dichloromethane-1.3% methanol). $^1$H NMR (400 MHz, DMSO-$d_6$): 1.46 (3H, s), 2.37 (3H, s), 4.15 (1H, d, J=10.1 Hz), 4.39 (1H, d, J=10.1 Hz), 6.51 (1H, s), 7.10 (1H, dd, J=8.8 Hz, J=2.4 Hz), 7.37 (1H, d, J=2.4 Hz), 7.86 (1H, d, J=8.8 Hz), 8.05-8.12 (2H, m), 8.18 (1H, d, J=2.3 Hz), 9.56 (1H, s).

Example 66

3-(4-Cyano-3-fluorophenoxy)-N-(3-formyl-4-nitrophenyl)-2-hydroxy-2-methylpropionamide 3-(4-Cyano-3-fluorophenoxy)-2-hydroxy-N-(3-hydroxymethyl-4-nitrophenyl)-2-methylpropionamide (0.2 g, 0.51 mmol) was dissolved in dichloromethane (10 ml) and manganese(IV) oxide (0.4 g, 4.6 mmol) was added. The mixture was stirred at room temperature for 48 hours. The solid oxidant was removed by filtration and the solvent was evaporated. The crude product was purified by flash chromatography (dichloromethane-3% methanol). $^1$H NMR (400 MHz, DMSO-$d_6$): 1.45 (3H, s), 4.13 (1H, d, J=10.0 Hz), 4.38 (1H, d, J=10.0 Hz), 6.32 (1H, s), 6.94-6.97 (1H, m), 7.16-7.20 (1H, m), 7.77-7.82 (1H, m), 8.18-8.24 (2H, m), 8.36 (1H, d, J=2.1 Hz), 10.28 (1H, s), 10.55 (1H, s).

Example 67

3-[4-(2-Dimethylaminoethoxy)phenoxy]-2-hydroxy-2-methyl-N-(3-methyl-4-nitrophenyl)propionamide a) [2-(4-Benzyloxyphenoxy)ethyl]dimethylamine 4-(Benzyloxy)phenol (2.89 g, 0.01443 mol) in dimethylformamide (15 ml) and 2-(dimethylamino)ethyl chloride hydrochloride (2.32 g, 0.01611 mol) were added simultaneously in small portions to a 55-65% sodium hydride dispersion in mineral oil (0.033 mol) in dimethylformamide (5 ml) at 0° C. Then the mixture was allowed to warm to 90° C., and stirring was continued for 1.5 h. The cooled mixture was poured into water. The resultant mixture was extracted with toluene. The combined extracts were washed with 2.5 M NaOH and water and dried over $Na_2SO_4$. Toluene was evaporated and the residual product was used as such in the next step.

$^1$H NMR (300 MHz, DMSO-$d_6$): 2.20 (6H, s), 2.58 (2H, t, $^3$J=5.9 Hz), 3.96 (2H, t, $^3$J=5.9 Hz), 5.03 (2H, s), 6.85 (2H, d, $^3$J=9.3 Hz), 6.92 (2H, d, $^3$J=9.3 Hz), 7.30-7.44 (5H, m).

b) 4-(2-Dimethylaminoethoxy)phenol

A stirred solution of [2-(4-benzyloxyphenoxy)ethyl]dimethylamine (3.36 g, 0.01238 mol) in the mixture of 6 M HCl (67 ml) and ethanol (33.5 ml) was refluxed for 6.5 h. Then ethanol was evaporated and pH was adjusted to 8 with 2.5 M NaOH. The product was extracted into ethyl acetate. The extracts were washed with water and dried over $Na_2SO_4$. Removal of solvent under reduced pressure gave a raw product which was purified by flash chromatography on silica gel using heptane/ethyl acetate (9:1-6:4) as a gradient eluent. $^1$H NMR (300 MHz, DMSO-$d_6$): 2.20 (6H, s), 2.57 (2H, t, $^3J$=5.9 Hz), 3.92 (2H, t, $^3J$=5.9 Hz), 6.65 (2H, d, $^3J$=9.1 Hz), 6.74 (2H, d, $^3J$=9.0 Hz), 8.85 (1H, s, —OH).

c) 3-[4-(2-Dimethylaminoethoxy)phenoxy]-2-hydroxy-2-methyl-N-(3-methyl-4-nitrophenyl)propionamide 3-[4-(2-Dimethylaminoethoxy)phenoxy]-2-hydroxy-2-methyl-N-(3-methyl-4-nitrophenyl)propionamide was prepared as described in Example 1c starting from 4-(2-dimethylaminoethoxy)phenol and 2-methyloxirane-2-carbocylic acid (3-methyl-4-nitrophenyl)amide. The product was extracted at pH 8. The crude product was purified by flash chromatography using dichloromethane/methanol as a gradient eluent (methanol 0-20%). Crystallization from toluene. $^1$H NMR (400 MHz, DMSO-$d_6$): 1.42 (3H, s), 2.19 (6H, s), 2.53 (3H, s), 2.57 (2H, t, $^3J$=5.8 Hz), 3.90 (1H, d, $^2J_{gem}$=9.6 Hz), 3.95 (2H, t, $^3J$=5.9 Hz), 4.14 (1H, d, $^2J_{gem}$=9.5 Hz), 6.18 (1H, s, —OH), 6.83 (4H, s), 7.88 (1H, dd, $^3J$=9.0 Hz, $^4J$=2.3 Hz), 7.93 (1H, d, $^4J$=1.8 Hz), 8.04 (1H, d, $^3J$=9.0 Hz), 10.14 (1H, s, —NHCO—).

Example 68

3-(4-Cyanomethylphenoxy)-2-hydroxy-2-methyl-N-(3-methyl-4-nitrophenyl)propionamide 3-(4-Cyanomethylphenoxy)-2-hydroxy-2-methyl-N-(3-methyl-4-nitrophenyl)propionamide was prepared as described in Example 1c starting from 4-hydroxy-benzyl cyanide and 2-methyloxirane-2-carbocylic acid (3-methyl-4-nitrophenyl)amide. The crude product was purified by flash chromatography using heptane/ethyl acetate as a gradient eluent (9:1-7:3). Crystallization from toluene, m.p. 143-145° C.

$^1$H NMR (300 MHz, DMSO-$d_6$): 1.43 (3H, s), 2.53 (3H, s), 3.92 (2H, s), 3.98 (1H, d, $^2J_{gem}$=9.7 Hz), 4.21 (1H, d, $^2J_{gem}$=9.7 Hz), 6.17 (1H, broad s, —OH), 6.94 (2H, d, $^3J$=8.7 Hz), 7.23 (2H, d, $^3J$=8.7 Hz), 7.87 (1H, dd, $^3J$=9.0 Hz, $^4J$=2.2 Hz), 7.92 (1H, s), 8.03 (1H, d, $^3J$=8.9 Hz), 10.09 (1H, broad s, —NHCO—).

Example 69

3-[4-(2-Chloroethyl)phenoxy]-2-hydroxy-2-methyl-N-(3-methyl-4-nitrophenyl)propionamide 3-[4-(2-Chloroethyl)phenoxy]-2-hydroxy-2-methyl-4-nitrophenyl)propionamide was prepared as described in Example 1c starting from 4-(2-chloroethyl)phenol (A. C. Spivey et al. J. Org. Chem. 65 (2000) 5253; P. G. Baraldi et al. J. Med. Chem. 45 (2002) 115) and 2-methyl-oxirane-2-carbocylic acid (3-methyl-4-nitrophenyl)amide. The crude product was purified twice by flash chromatography using first heptane/ethyl acetate as a gradient eluent (9:1-8:2) and then only dichloromethane. $^1$H NMR (400 MHz, DMSO-$d_6$): 1.43 (3H, s), 2.53 (3H, s), 2.93 (2H, t, $^3J$=7.1 Hz), 3.77 (2H, t, $^3J$=7.1 Hz), 3.95 (1H, d, $^2J_{gem}$=9.6 Hz), 4.19 (1H, d, $^2J_{gem}$=9.6 Hz), about 6.2 (1H, broad s, —OH), 6.85 (2H, d, $^3J$=8.6 Hz), 7.16 (2H, d, $^3J$=8.7 Hz), 7.89 (1H, dd, $^3J$=9.0 Hz, $^4J$=2.3 Hz), 7.94 (1H, d, $^4J$=2.2 Hz), 8.04 (1H, d, $^3J$=9.0 Hz), about 10.2 (1H, broad s, —NHCO—).

Example 70

2-Hydroxy-3-(4-hydroxymethylphenoxy)-2-methyl-N-(3-methyl-4-nitrophenyl)propionamide 2-Hydroxy-3-(4-hydroxymethylphenoxy)-2-methyl-N-(3-methyl-4-nitrophenyl)propionamide was prepared as described in Example 1c starting from 4-hydroxybenzyl alcohol and 2-methyloxirane-2-carbocylic acid (3-methyl-4-nitrophenyl)amide. The crude product was purified by flash chromatography using heptane/ethyl acetate as a gradient eluent (95:5-25:75). $^1$H NMR (400 MHz, DMSO-$d_6$): 1.43 (3H, s), 2.53 (3H, s), 3.95 (1H, d, $^2J_{gem}$=9.6 Hz), 4.18 (1H, d, $^2J_{gem}$=9.6 Hz), 4.39 (2H, d, $^3J$=5.3 Hz), 5.05 (1H, t, $^3J$=5.7 Hz), 6.22 (1H, s, —OH), 6.86 (2H, d, $^3J$=8.6 Hz), 7.19 (2H, d, $^3J$=8.8 Hz), 7.89 (1H, dd, $^3J$=9.0 Hz, $^4J$=2.3 Hz), 7.94 (1H, d, $^4J$=2.2 Hz), 8.04 (1H, d, $^3J$=9.0 Hz), 10.16 (1H, s, —NHCO—).

Example 71

2-Hydroxy-3-(4-hydroxyphenoxy)-2-methyl-N-(3-methylnitrophenyl)propionamide 2-Hydroxy-3-(4-hydroxyphenoxy)-2-methyl-N-(3-methyl-4-nitrophenyl)propionamide was prepared as described in Example 1c starting from hydroquinone and 2-methyloxirane-2-carbocylic acid (3-methyl-4-nitrophenyl)amide. The crude product was purified by flash chromatography using heptane/ethyl acetate as a gradient eluent (9:1-6:4). $^1$H NMR (400 MHz, DMSO-$d_6$): 1.40 (3H, s), 2.53 (3H, s), 3.86 (1H, d, $^2J_{gem}$=9.4 Hz), 4.10 (1H, d, $^2J_{gem}$=9.4 Hz), 5.76 (1H, broad s, —OH), 6.63 (2H, d, $^3J$=9.0 Hz), 6.73 (2H, d, $^3J$=9.0 Hz), 7.88 (1H, dd, $^3J$=9.0 Hz, $^4J$=2.4 Hz), 7.93 (1H, d, $^4J$=2.1 Hz), 8.04 (1H, d, $^3J$=9.0 Hz), 8.92 (1H, broad s, ArO<u>H</u>), 10.13 (1H, broad s, —NHCO—).

Example 72

3-(3-Cyanophenoxy)-2-hydroxy-2-methyl-N-(3-methyl-4-nitrophenyl)propionamide 3-(3-Cyanophenoxy)-2-hydroxy-2-methyl-N-(3-methyl-4-nitrophenyl)propionamide was prepared as described in Example 1c starting from 3-cyanophenol and 2-methyloxirane-2-carbocylic acid (3-methyl-4-nitrophenyl)amide. The crude product was purified by flash chromatography using heptane/ethyl acetate as a gradient eluent. Crystallization from toluene, m.p. 107-110° C. $^1$H NMR (300 MHz, DMSO-$d_6$): 1.44 (3H, s), 2.53 (3H, s), 4.06 (1H, d, $^2J_{gem}$=10.0 Hz), 4.31 (1H, d, $^2J_{gem}$=9.9 Hz), about 6.3 (1H, broad s, —OH), 7.27 (1H, m), 7.38 (1H, dt, $^3J$=7.5 Hz, $^4J$=1.3 Hz), 7.43 (1H, m), 7.46 (1H, t, $^3J$=7.8 Hz), 7.87 (1H, dd, $^3J$=9.0 Hz, $^4J$=2.3 Hz), 7.91 (1H, d, $^4J$=9.0 Hz, $^4J$=1.9 Hz), 8.03 (1H, d, $^3J$=9.0 Hz), about 10.1 (1H, broad s, —NHCO—).

Example 73

3-(3-Fluoro-5-trifluoromethylphenoxy)-2-hydroxy-2-methyl-N-(3-methyl-4-nitrophenyl)propionamide

3-(3-Fluoro-5-trifluoromethylphenoxy)-2-hydroxy-2-methyl-N-(3-methyl-4-nitrophenyl)propionamide was prepared as described in Example 1c starting from 3-fluoro-5-(trifluoromethyl)phenol and 2-methyloxirane-2-carbocylic acid (3-methyl-4-nitrophenyl)amide. The crude product was purified by flash chromatography using heptane/ethyl acetate as a gradient eluent. Crystallization from toluene/heptane. $^1$H NMR (400 MHz, DMSO-$d_6$): 1.44 (3H, s), 2.53 (3H, s), 4.15 (1H, d, $^2J_{gem}$=10.0 Hz), 4.37 (1H, d, $^2J_{gem}$=10.0 Hz), 6.26 (1H, broad s, —OH), 7.12 (1H, s), 7.19-7.22 (2H, m), 7.87 (1H, dd, $^3J$=8.9 Hz, $^4J$=2.3 Hz), 7.92 (1H, d, $^4J$=1.9 Hz), 8.03 (1H, d, $^3J$=9.0 Hz), 10.15 (1H, broad s, —NHCO—).

Example 74

3-(3,5-Difluorophenoxy)-2-hydroxy-2-methyl-N-(3-methyl-4-nitrophenyl)propionamide

3-(3,5-Difluorophenoxy)-2-hydroxy-2-methyl-N-(3-methyl-4-nitrophenyl)propionamide was prepared as described in Example 1c starting from 3,5-difluorophenol and 2-methyloxirane-2-carbocylic acid (3-methyl-4-nitrophenyl)amide. The crude product was purified by flash chromatography using heptane/ethyl acetate as a gradient eluent (95:5-70:30). Crystallization from toluene, m.p. 104-106° C. $^1$H NMR (400 MHz, DMSO-$d_6$): 1.43 (3H, s), 2.53 (3H, s), 4.01 (1H, d, $^2J_{gem}$=9.9 Hz), 4.27 (1H, d, $^2J_{gem}$=9.8 Hz), about 6.3 (1H, broad s, —OH), 6.71 (2H, dd, $^3J_{HF}$=9.5 Hz, $^4J_{HH}$=2.1 Hz), 6.76 (1H, tt, $^3J_{HF}$=9.4 Hz, $^4J_{HH}$=2.3 Hz), 7.87 (1H, dd, $^3J$=9.0 Hz, $^4J$=2.4 Hz), 7.92 (1H, d, $^4J$=2.2 Hz), 8.04 (1H, d, $^3J$=9.0 Hz), about 10.1 (1H, broad s, —NHCO—).

Example 75

3-(2,3-Difluorophenoxy)-2-hydroxy-2-methyl-N-(3-methyl-4-nitrophenyl)propionamide

3-(2,3-Difluorophenoxy)-2-hydroxy-2-methyl-N-(3-methyl-4-nitrophenyl)propionamide was prepared as described in Example 1c starting from 2,3-difluorophenol and 2-methyloxirane-2-carbocylic acid (3-methyl-4-nitrophenyl)amide. The crude product was purified twice by flash chromatography using first heptane/ethyl acetate (8:2) and then dichloromethane as an eluent. Trituration in heptane, m.p. 68-73° C. $^1$H NMR (300 MHz, DMSO-$d_6$): 1.44 (3H, s), 2.53 (3H, s), 4.11 (1H, d, $^2J_{gem}$=9.9 Hz), 4.31 (1H, d, $^2J_{gem}$=9.8 Hz), 6.28 (1H, s, —OH), 6.93-7.14 (3H, m), 7.86 (1H, dd, $^3J$=8.9 Hz, $^4J$=2.3 Hz), 7.91 (1H, d, $^4J$=2.1 Hz), 8.03 (1H, d, $^3J$=8.9 Hz), 10.15 (1H, s, —NHCO—).

Example 76

3-(2,6-Difluorophenoxy)-2-hydroxy-2-methyl-N-(3-methyl-4-nitrophenyl)propionamide

3-(2,6-Difluorophenoxy)-2-hydroxy-2-methyl-N-(3-methyl-4-nitrophenyl)propionamide was prepared as described in Example 1c starting from 2,6-difluorophenol and 2-methyloxirane-2-carbocylic acid (3-methyl-4-nitrophenyl)amide. The crude product was purified by flash chromatography using heptane/ethyl acetate as a gradient eluent (9:1-7:3). $^1$H NMR (400 MHz, DMSO-$d_6$): 1.40 (3H, s), 2.53 (3H, s), 4.16 (1H, d, $^2J_{gem}$=10.0 Hz), 4.31 (1H, d, $^2J_{gem}$=10.0 Hz), 6.18 (1H, broad s, —OH), 7.06-7.12 (3H, m), 7.86 (1H, dd, $^3J$=8.9 Hz, $^4J$=2.3 Hz), 7.88 (1H, d, $^4J$=2.3 Hz), 8.04 (1H, d, $^3J$=8.8 Hz), 10.08 (1H, broad s, —NHCO—)

Example 77

2-Hydroxy-2-methyl-N-(3-methyl-4-nitrophenyl)-3-(3-trifluoromethyl-phenoxy)propionamide

2-Hydroxy-2-methyl-N-(3-methyl-4-nitrophenyl)-3-(3-trifluoromethyl-phenoxy)propionamide was prepared as described in Example 1c starting from 3-hydroxybenzotrifluoride and 2-methyloxirane-2-carbocylic acid (3-methyl-4-nitrophenyl)amide. The crude product was purified by flash chromatography using heptane/ethyl acetate as a gradient eluent (9:1-5:5). Crystallization from CH$_2$Cl$_2$/EtOH/heptane, m.p. 84-87° C. $^1$H NMR (400 MHz, DMSO-$d_6$): 1.45 (3H, s), 2.53 (3H, s), 4.07 (1H, d, $^2J_{gem}$=9.8 Hz), 4.33 (1H, d, $^2J_{gem}$=9.8 Hz), 6.25 (1H, broad s, —OH), 7.23 (1H, s), 7.24 (1H, d, $^3J$=6.7 Hz,), 7.28 (1H, d, $^3J$=7.7 Hz,), 7.50 (1H, t, $^3J$=8.3 Hz,), 7.88 (1H, dd, $^3J$=8.9 Hz, $^4J$=2.3 Hz), 7.92 (1H, d, $^4J$=2.0 Hz), 8.03 (1H, d, $^3J$=9.0 Hz), 10.15 (1H, broad s, —NHCO—).

Example 78

3-(3,5-Dichlorophenoxy)-2-hydroxy-2-methyl-N-(3-methyl-4-nitrophenyl)propionamide

3-(3,5-Dichlorophenoxy)-2-hydroxy-2-methyl-N-(3-methyl-4-nitrophenyl)propionamide was prepared as described in Example 1c starting from 3,5-dichlorophenol and 2-methyloxirane-2-carbocylic acid (3-methyl-4-nitrophenyl)amide. The crude product was purified by flash chromatography using heptane/ethyl acetate as an eluent (9:1). Crystallization from toluene, m.p. 141-143° C. $^1$H NMR (400 MHz, DMSO-$d_6$): 1.42 (3H, s), 2.53 (3H, s), 4.05 (1H, d, $^2J_{gem}$=10.1 Hz), 4.31 (1H, d, $^2J_{gem}$=10.1 Hz), about 6.2 (1H, broad s, —OH), 7.04 (2H, distorted d, $^4J$=1.9 Hz), 7.13 (1H, distorted t, $^4J$=1.7 Hz), 7.87 (1H, d, $^3J$=8.9 Hz), 7.92 (1H, s), 8.04 (1H, d, $^3J$=8.90 Hz), about 10.1 (1H, broad s, —NHCO—).

Example 79

3-[4-(3-Chloropropyl)phenoxy]-2-hydroxy-2-methyl-N-(3-methyl-4-nitrophenyl)propionamide a) 4-(3-Chloropropyl)phenol 3-(4-Hydroxyphenyl)-1-propanol (0.97 g, 0.006374 mol) and concentrated HCl (20 ml) were heated at 100° C. for 14 h. After being cooled, the reaction mixture was poured into water and extracted with ethyl acetate. The extracts were washed with water, dried and concentrated in vacuo to give a raw product. Purification by flash chromatography (heptane/ethyl acetate 9:1) gave a pure product (0.98 g, 90%).
$^1$H NMR (400 MHz, DMSO-$d_6$): 1.95 (2H, quintet, $^3J$=7.0 Hz), 2.59 (2H, t, $^3J$=7.5 Hz), 3.58 (2H, t, $^3J$=6.5 Hz), 6.67 (2H, d, $^3J$=8.2 Hz), 6.99 (2H, d, $^3J$=8.2 Hz), 9.15 (1H, s, —OH).

b) 3-[4-(3-Chloropropyl)phenoxy]-2-hydroxy-2-methyl-N-(3-methyl-4-nitrophenyl)propionamide 3-[4-(3-Chloropropyl)phenoxy]-2-hydroxy-2-methyl-N-(3-methyl-4-nitrophenyl)propionamide was prepared as described in Example 1c starting from 4-(3-chloropropyl) phenol and 2-methyloxirane-2-carbocylic acid (3-methyl-4-nitrophenyl)amide. Purification twice by flash chromatography (first only dichloromethane and then heptane/ethyl acetate 9:1 as an eluent) gave a pure product, m.p. 110-112° C. $^1$H NMR (400 MHz, DMSO-d$_6$): 1.43 (3H, s), 1.95 (2H, quintet, $^3$J=7.0 Hz), 2.53 (3H, s), 2.62 (2H, t, $^3$J=7.4 Hz), 3.58 (2H, t, $^3$J=6.5 Hz), 3.95 (1H, d, $^2$J$_{gem}$=9.6 Hz), 4.18 (1H, d, $^2$J$_{gem}$=9.5 Hz), 6.15 (1H, broad s, —OH), 6.84 (2H, d, $^3$J=8.5 Hz), 7.10 (2H, d, $^3$J=8.4 Hz), 7.88 (1H, d, $^3$J=9.1 Hz), 7.93 (1H, s), 8.03 (1H, d, $^3$J=9.0 Hz), 10.14 (1H, broad s, —NHCO—).

Example 80

3-[4-(2-Chloroethoxy)phenoxy]-2-hydroxy-2-methyl-N-(3-methyl-4-nitrophenyl)propionamide 3-[4-(2-Chloroethoxy)phenoxy]-2-hydroxy-2-methyl-N-(3-methyl-4-nitrophenyl)propionamide was prepared as described in Example 1c starting from 4-(2-chloroethoxy) phenol (H. K. A. C. Coolen et al., Recueil des Travaux Chimiques des Pays-Bas 114(2) (1995) 65) and 2-methyloxirane-2-carbocylic acid (3-methyl-4-nitrophenyl)amide. The crude product was purified by flash chromatography using heptane/ethyl acetate (75:25) as an eluent, m.p. 131-133° C. $^1$H NMR (400 MHz, DMSO-d$_6$): 1.42 (3H, s), 2.53 (3H, s), 3.88-3.93 (3H, m), 4.14-4.18 (3H, m), about 6.2 (1H, broad s, —OH), 6.86 (4H, s), 7.88 (1H, d, $^3$J=9.0 Hz), 7.92 (1H, s), 8.04 (1H, d, $^3$J=9.0 Hz), about 10.1 (1H, broad s, —NHCO—).

Example 81

2-Hydroxy-3-(4-methoxymethylphenoxy)-2-methyl-N-(3-methyl-4-nitrophenyl)propionamide 2-Hydroxy-3-(4-methoxymethylphenoxy)-2-methyl-N-(3-methyl-4-nitrophenyl)propionamide was prepared as described in Example 1c starting from 4-(methoxymethyl) phenol (J. M. Saá et al., J. Org. Chem. 53 (1988) 4263; D. R. Dimmel and D. Shepard, J. Org. Chem. 47 (1982) 22) and 2-methyloxirane-2-carbocylic acid (3-methyl-4-nitrophenyl) amide. The crude product was purified by using flash chromatography several times (dichloromethane/methanol 99:1, heptane/ethyl acetate as a gradient eluent (9:1-7:3), dichloromethane/methanol 99.5:0.5). $^1$H NMR (400 MHz, DMSO-d$_6$): 1.43 (3H, s), 2.53 (3H, s), 3.22 (3H, s), 3.97 (1H, d, $^2$J$_{gem}$=9.6 Hz), 4.20 (1H, d, $^2$J$_{gem}$=9.5 Hz), 4.30 (2H, s), 6.19 (1H, broad s, —OH), 6.89 (2H, d, $^3$J=7.9 Hz), 7.20 (2H, d, $^3$J=8.2 Hz), 7.88 (1H, d, $^3$J=9.0 Hz), 7.93 (1H, s), 8.04 (1H, d, $^3$J=9.0 Hz), 10.13 (1H, broad s, —NHCO—).

Example 82

3-[4-(2-Fluoroethyl)phenoxy]-2-hydroxy-2-methyl-N-(3-methyl-4-nitrophenyl)propionamide A solution of 2-hydroxy-3-[4-(2-hydroxyethylphenoxy]-2-methyl-N-(3-methyl-4-nitrophenyl)propionamide (prepared in Example 20, 300 mg, 0.0008012 mol) in dry CH$_2$Cl$_2$ (3 ml) was treated with Deoxo-Fluor® (195 mg, 0.0008813 mol) in dry CH$_2$Cl$_2$ (1 ml) at −15 to −10° C. The solution was stirred for 2 h at 0° C. and then for 3 days at room temperature. The saturated NaHCO$_3$ solution was added and the mixture was extracted with dichloromethane. The combined extracts were washed with water, dried over Na$_2$SO$_4$, filtered, and evaporated in vacuo. The crude product was purified by flash chromatography using dichloromethane as an eluent. Crystallization from toluene afforded the desired compound as pure crystals: m.p. 102-105° C. $^1$H NMR (400 MHz, DMSO-d$_6$): 1.43 (3H, s), 2.53 (3H, s), 2.88 (2H, dt, $^3$J$_{HF}$=24.4 Hz, $^3$J=6.4 Hz), 3.95 (1H, d, $^2$J$_{gem}$=9.8 Hz), 4.18 (1H, d, $^2$J$_{gem}$=9.5 Hz), 4.56 (2H, dt, $^2$J$_{HF}$=47.4 Hz, $^3$J=6.4 Hz), 6.18 (1H, broad s, —OH), 6.85 (2H, d, $^3$J=8.5 Hz), 7.15 (2H, d, $^3$J=8.4 Hz), 7.88 (1H, d, $^3$J=9.0 Hz), 7.93 (1H, s), 8.03 (1H, d, $^3$J=9.0 Hz), 10.13 (1H, broad s, —NHCO—).

Example 83

3-(4-Fluoromethylphenoxy)-2-hydroxy-2-methyl-N-(3-methyl-4-nitrophenyl)propionamide A solution of 2-hydroxy-3-(4-hydroxymethylphenoxy)-2-methyl-N-(3-methyl-4-nitrophenyl)propionamide (prepared in Example 70, 950 mg, 0.002636 mol) in dry CH$_2$Cl$_2$ (6.5 ml) was treated with Deoxo-Fluor® (875 mg, 0.003954 mol) in CH$_2$Cl$_2$ (3 ml) at −76° C. The solution was stirred at −10° C. for 3 hours. The saturated NaHCO$_3$ solution was added and the mixture was extracted with dichloromethane. The combined extracts were washed with water, dried over Na$_2$SO$_4$, filtered, and evaporated in vacuo. The crude product was purified by flash chromatography using heptane/ethyl acetate as a gradient eluent (9:1-5:5). Crystallization from dichloromethane/heptane gave the desired compound. $^1$H NMR (400 MHz, DMSO-d$_6$): 1.44 (3H, s), 2.53 (3H, s), 4.00 (1H, d, $^2$J$_{gem}$=9.7 Hz), 4.24 (1H, d, $^2$J$_{gem}$=9.6 Hz), 5.30 (2H, d, $^2$J$_{HF}$=48.6 Hz), 6.21 (1H, s, —OH), 6.95 (2H, d, $^3$J=8.4 Hz), 7.34 (2H, d, $^3$J=8.6 Hz), 7.84 (1H, dd, $^3$J=9.0 Hz, $^4$J=2.0 Hz), 7.93 (1H, broad s), 8.03 (1H, d, $^3$J=9.0 Hz), 10.14 (1H, s, —NHCO—).

Example 84

3-[4-(2-Bromoethyl)phenoxy]-2-hydroxy-2-methyl-N-(3-methyl-4-nitrophenyl)propionamide a) 4-(2-Bromoethyl)phenol (4-Hydroxyphenethyl) alcohol (1.50 g, 0.01086 mol) and 48 wt. % hydrobromic acid (10 ml) were heated at 100° C. for 1.5 h. After being cooled, the reaction mixture was poured into water and extracted with ethyl acetate. The extracts were washed with water, dried and concentrated in vacuo to give a raw product. Purification by flash chromatography (heptane/ethyl acetate 9:1) gave a pure product (2.01 g, 92%). $^1$H NMR (400 MHz, DMSO-d$_6$): 2.99 (2H, t, $^3$J=7.4 Hz), 3.63 (2H, t, $^3$J=7.4 Hz), 6.68 (2H, d, $^3$J=8.5 Hz), 7.05 (2H, d, $^3$J=8.3 Hz), 9.24 (1H, s, —OH).

b) 3-[4-(2-Bromoethyl)phenoxy]-2-hydroxy-2-methyl-N-(3-methyl-4-nitrophenyl)propionamide 3-[4-(2-Bromoethyl)phenoxy]-2-hydroxy-2-methyl-N-(3-methyl-4-nitrophenyl)propionamide was prepared as described in Example 1c starting from 4-(2-bromoethyl)phenol and 2-methyloxirane-2-carbocylic acid (3-methyl-4-nitrophenyl)amide. Purification by flash chromatography on silica gel (dichloromethane/methanol 99:1 or toluene/methanol 99.5:0.5 gave an impure product. The final purification was made by preparative HPLC. $^1$H NMR (400 MHz, CDCl$_3$): 1.59 (3H, s), 2.63 (3H, s), 3.10 (2H, t, $^3$J=7.5 Hz), about 3.5 (—OH), 3.52 (2H, t, $^3$J=7.4 Hz), 3.98 (1H, d, $^2$J$_{gem}$=9.0 Hz), 4.44 (1H, d, $^2$J$_{gem}$=9.0 Hz), 6.87 (2H, d, $^3$J=8.6

Hz), 7.13 (2H, d, $^3J$=8.6 Hz), 7.57 (1H, dd, $^3J$=8.9 Hz, $^4J$=2.3 Hz), 7.65 (1H, d, $^4J$=2.2 Hz), 8.06 (1H, d, $^3J$=8.9 Hz), 9.00 (1H, s, —NHCO—).

Example 85

2-Hydroxy-3-[4-(2-iodoethyl)phenoxy]-2-methyl-N-(3-methyl-4-nitrophenyl)propionamide a) 4-(2-Iodoethyl)phenol Triphenylphosphine (1.57 g, 0.006 mol) and imidazole (0.41 g, 0.006 mol) were added to dry dichloromethane (20 ml). When the imidazole was in solution iodine (1.52 g, 0.006 mol) was added. After precipitation of the imidazole hydroiodide (4-hydroxyphenethyl) alcohol (0.69 g, 0.005 mol) was added. The mixture was stirred at room temperature for 4 h. Then water was added and the mixture was extracted with dichloromethane. The extracts were washed with water, dried and concentrated in vacuo to give a raw product. Purification by flash chromatography (heptane/ethyl acetate as a gradient eluent 9:1-6:4) gave a pure product. $^1$H NMR (400 MHz, DMSO-$d_6$): 2.99 (2H, t, $^3J$=7.6 Hz), 3.38 (2H, t, $^3J$=7.6 Hz), 6.68 (2H, d, $^3J$=8.5 Hz), 7.03 (2H, d, $^3J$=8.5 Hz), 9.24 (1H, s, —OH).

b) 2-Hydroxy-3-[4-(2-iodoethyl)phenoxy]-2-methyl-N-(3-methyl-4-nitrophenyl)propionamide 2-Hydroxy-3-[4-(2-iodoethyl)phenoxy]-2-methyl-N-(3-methyl-4-nitrophenyl)propionamide was prepared as described in Example 1c starting from 4-(2-iodoethyl)phenol and 2-methyloxirane-2-carbocylic acid (3-methyl-4-nitrophenyl)amide. Purification by flash chromatography on silica gel (heptane/ethyl acetate as a gradient eluent 9:1-6:4) gave an impure product. The final purification was made by preparative HPLC. $^1$H NMR (400 MHz, DMSO-$d_6$): 1.43 (3H, s), 2.53 (3H, s), 3.03 (2H, t, $^3J$=7.4 Hz), 3.40 (2H, t, $^3J$=7.4 Hz), 3.96 (1H, d, $^2J_{gem}$=9.6 Hz), 4.19 (1H, d, $^2J_{gem}$=9.6 Hz), 6.17 (1H, s, —OH), 6.85 (2H, d, $^3J$=8.6 Hz), 7.14 (2H, d, $^3J$=8.6 Hz), 7.88 (1H, dd, $^3J$=9.0 Hz, $^4J$=2.2 Hz), 7.93 (1H, d, $^4J$=2.0 Hz), 8.03 (1H, d, $^3J$=9.0 Hz), 10.13 (1H, s, —NHCO—).

Example 86

3-[4-(2-Bromoethoxy)phenoxy]-2-hydroxy-2-methyl-N-(3-methyl-4-nitrophenyl)propionamide a) 4-(2-Bromoethoxy)phenol Potassium carbonate (7.53 g, 0.05448 mol) was added to the acetone solution (50 ml) of hydroquinone (2.00 g, 0.01816 mol) and 1,2-dibromoethane (3.39 g, 0.01805 mol). The mixture was heated at reflux for 6 h under nitrogen. The resulting mixture was filtered, water was added and pH was adjusted to 2-3. The mixture was extracted with ethyl acetate. The extracts were washed with water, dried over anhydrous Na$_2$SO$_4$, filtered and evaporated. The crude product was purified by flash chromatography on silica gel, using heptane/ethyl acetate as a gradient eluent (95:5-70:30) to afford the pure desired compound as white crystals. $^1$H NMR (400 MHz, DMSO-$d_6$): 3.74 (2H, t, $^3J$=5.5 Hz), 4.19 (2H, t, $^3J$=5.5 Hz), 6.67 (2H, d, $^3J$=8.9 Hz), 6.78 (2H, d, $^3J$=8.9 Hz), 8.95 (1H, s, —OH).

b) 3-[4-(2-Bromoethoxy)phenoxy]-2-hydroxy-2-methyl-N-(3-methyl-4-nitrophenyl)propionamide 3-[4-(2-Bromoethoxy)phenoxy]-2-hydroxy-2-methyl-N-(3-methyl-4-nitrophenyl)propionamide was prepared as described in Example 1c starting from 4-(2-bromoethoxy) phenol and 2-methyl-oxirane-2-carbocylic acid (3-methyl-4-nitrophenyl)amide. The crude product was purified by flash chromatography on silica gel, using heptane/ethyl acetate as a gradient eluent (9:1-6:4). The desired compound was crystallized from dichloromethane, m.p. 135-138° C. $^1$H NMR (400 MHz, DMSO-$d_6$): 1.42 (3H, s), 2.53 (3H, s), 3.75 (2H, t, $^3J$=5.5 Hz), 3.92 (1H, d, $^2J_{gem}$=9.6 Hz), 4.15 (1H, d, $^2J_{gem}$=9.5 Hz), 4.23 (2H, t, $^3J$=5.4 Hz), 6.16 (1H, broad s, —OH), 6.86 (4H, s), 7.88 (1H, dd, $^3J$=9.0 Hz, $^4J$=2.2 Hz), 7.92 (1H, d, $^4J$=1.7 Hz), 8.04 (1H, d, $^3J$=8.9 Hz), 10.12 (1H, broad s, —NHCO—).

Example 87

3-[4-(2-Chloroethyl)-3-fluorophenoxy]-2-hydroxy-2-methyl-N-(3-methyl-4-nitrophenyl)propionamide a) 3-Fluoro-4-(2-hydroxyethyl)phenol Borane-tetrahydrofuran complex (1.0 M solution in THF, 22 ml, 0.02200 mol) was added dropwise to the solution of (2-fluoro-4-hydroxyphenyl)acetic acid (P. C. Belanger et al. EP 106565 B1, 2.27 g, 0.01145 mol) in dry THF (40 ml) under nitrogen at −10° C., and the resulting solution was stirred for 2 h at −10° C. Water was added and the product was extracted into ethyl acetate. The combined extracts were washed with water, dried and evaporated in vacuo to give the product. $^1$H NMR (400 MHz, DMSO-$d_6$): 2.62 (2H, t, $^3J$=7.2 Hz), 3.50 (2H, m), 4.63 (1H, t, $^3J$=5.4 Hz, —CH$_2$OH), 6.47-6.53 (2H, m), 7.06 (1H, t, $^3J_{HH}$=$^4J_{HF}$=8.5 Hz), 9.60 (1H, s, ArOH).

b) 4-(2-Chloroethyl)-3-fluorophenol 4-(2-Chloroethyl)-3-fluorophenol was prepared as described in Example 74a starting from 3-fluoro-4-(2-hydroxyethyl)phenol. The crude product was purified by flash chromatography using heptane/ethyl acetate as an eluent (85:15). $^1$H NMR (400 MHz, DMSO-$d_6$): 2.93 (2H, t, $^3J$=7.1 Hz), 3.74 (2H, t, $^3J$=7.1 Hz), 6.51-6.57 (2H, m), 7.13 (1H, t, $^3J_{HH}$=$^4J_{HF}$=8.7 Hz), 9.75 (1H, s, ArOH).

c) 3-[4-(2-Chloroethyl)-3-fluorophenoxy]-2-hydroxy-2-methyl-N-(3-methyl-4-nitrophenyl)propionamide 3-[4-(2-Chloroethyl)-3-fluorophenoxy]-2-hydroxy-2-methyl-N-(3-methyl-4-nitrophenyl)propionamide was prepared as described in Example 1c starting from 4-(2-chloroethyl)-3-fluorophenol and 2-methyloxirane-2-carbocylic acid (3-methyl-4-nitrophenyl)amide. The crude product was purified by flash chromatography using dichloromethane as an eluent. The product was crystallized from dichloromethane-/heptane: m.p. 77-79° C. $^1$H NMR (400 MHz, DMSO-$d_6$): 1.43 (3H, s), 2.53 (3H, s), 2.97 (2H, t, $^3J$=6.9 Hz), 3.76 (2H, t, $^3J$=7.0 Hz), 3.98 (1H, d, $^2J_{gem}$=9.8 Hz), 4.23 (1H, d, $^2J_{gem}$=9.7 Hz), about 6.2 (1H, broad s, —OH), 6.73 (1H, dd, $^3J$=8.5 Hz, $^4J$=2.4 Hz), 6.80 (1H, dd, $^3J_{HF}$=12.1 Hz, $^4J_{HH}$=2.5 Hz), 7.24 (1H, t, $^3J_{HH}$=$^4J_{HF}$=8.8 Hz), 7.87 (1H, dd, $^3J$=9.0 Hz, $^4J$=2.3 Hz), 7.92 (1H, d, $^4J$=2.0 Hz), 8.03 (1H, d, $^3J$=9.0 Hz), about 10.1 (1H, broad s, —NHCO—).

Example 88

3-(4-Cyanophenoxy)-N-(3-ethyl-4-nitrophenyl)-2-hydroxy-2-methylpropionamide a) N-(3-Ethyl-4-nitrophenyl)-2-methylacrylamide

N-(3-Ethyl-4-nitrophenyl)-2-methylacrylamide was prepared as described in Example 1a starting from 3-ethyl-4-nitrophenylamine (W. Pfleiderer et al. U.S. 2002/0146737 A1) and methacryloyl chloride. The crude product was purified by flash chromatography using heptane/ethyl acetate (9:1) as an eluent. $^1$H NMR (400 MHz, DMSO-$d_6$): 1.22 (3H, t, $^3J$=7.4 Hz), 1.97 (3H, s), 2.87 (2H, q, $^3J$=7.4 Hz), 5.62 (1H, s), 5.88 (1H, s), 7.81 (1H, dd, $^3J$=8.9 Hz, $^4J$=2.3 Hz), 7.83 (1H, d, $^4J$=2.2 Hz), 8.00 (1H, d, $^3J$=8.8 Hz), 10.21 (1H, s, —NHCO—).

b) 2-Methyloxirane-2-carboxylic acid (3-ethyl-4-nitrophenyl)amide

3-Chloroperoxybenzoic acid (14.71 g, 0.08524 mol) was added in portions to the refluxing solution of N-(3-ethyl-4-nitrophenyl)-2-methylacrylamide (6.68 g, 0.02852 mol) and 2,6-di-tert-butyl-4-methylphenol (149 mg) in dichloromethane (180 ml). After refluxing for 5 h the reaction mixture was allowed to cool to room temperature. The precipitated 3-chlorobenzoic acid was filtered, and the filtrate was extracted three times with 1M $Na_2CO_3$ and water. The organic phase was dried over $Na_2SO_4$, filtered and evaporated. The crude product was purified by flash chromatography using dichloromethane as an eluent. $^1$H NMR (400 MHz, DMSO-$d_6$): 1.20 (3H, t, $^3J$=7.4 Hz), 1.55 (3H, s), 2.84 (2H, q, $^3J$=7.4 Hz), 2.99 (1H, d, $^2J_{gem}$=5.1 Hz), 3.06 (1H, d, $^2J_{gem}$=5.1 Hz), 7.81 (1H, dd, $^3J$=9.0 Hz, $^4J$=2.3 Hz), 7.85 (1H, d, $^4J$=2.2 Hz), 7.97 (1H, d, $^3J$=9.0 Hz), 9.88 (1H, s, —NHCO—).

c) 3-(4-Cyanophenoxy)-N-(3-ethyl-4-nitrophenyl)-2-hydroxy-2-methylpropionamide 3-(4-Cyanophenoxy)-N-(3-ethyl-4-nitrophenyl)-2-hydroxy-2-methylpropionamide was prepared as described in Example 1c starting from 4-cyanophenol and 2-methyloxirane-2-carbocylic acid (3-ethyl-4-nitrophenyl)amide. The crude product was purified by flash chromatography using heptane/ethyl acetate as a gradient eluent (9:1-6:4). $^1$H NMR (400 MHz, DMSO-$d_6$): 1.21 (3H, t, $^3J$=7.4 Hz), 1.45 (3H, s), 2.86 (2H, q, $^3J$=7.5 Hz), 4.09 (1H, d, $^2J_{gem}$=9.9 Hz), 4.33 (1H, d, $^2J_{gem}$=9.8 Hz), 6.26 (1H, broad s, —OH), 7.11 (2H, d, $^3J$=8.8 Hz), 7.74 (2H, d, $^3J$=8.7 Hz), 7.89 (1H, d, $^3J$=9.1 Hz), 7.94 (1H, s), 7.98 (1H, d, $^3J$=8.9 Hz), 10.17 (1H, broad s, —NHCO—).

Example 89

3-(4-Cyano-3-fluorophenoxy)-N-(3-ethyl-4-nitrophenyl)-2-hydroxy-2-methylpropionamide 3-(4-Cyano-3-fluorophenoxy)-N-(3-ethyl-4-nitrophenyl)-2-hydroxy-2-methylpropionamide was prepared as described in Example 1c starting from 2-fluoro-4-hydroxybenzonitrile and 2-methyl-oxirane-2-carbocylic acid (3-ethyl-4-nitrophenyl)amide. The crude product was purified twice by flash chromatography using heptane/ethyl acetate as a gradient eluent and the final purification was made by preparative HPLC. $^1$H NMR (400 MHz, DMSO-$d_6$): 1.21 (3H, t, $^3J$=7.4 Hz), 1.44 (3H, s), 2.86 (2H, q, $^3J$=7.5 Hz), 4.12 (1H, d, $^2J_{gem}$=10.0 Hz), 4.38 (1H, d, $^2J_{gem}$=10.0 Hz), 6.30 (1H, broad s, —OH), 6.96 (1H, dd, $^3J$=8.7 Hz, $^4J$=2.2 Hz), 7.18 (1H, dd, $^3J_{HF}$=11.8 Hz, $^4J_{HH}$=2.3 Hz), 7.80 (1H, t, $^3J_{HH}$=$^4J_{HF}$=8.3 Hz), 7.89 (1H, dd, $^3J$=8.9 Hz, $^4J$=2.2 Hz), 7.95 (1H, d, $^4J$=2.3 Hz), 7.98 (1H, d, $^3J$=9.0 Hz), 10.18 (1H, s, —NHCO—).

Example 90

2-Hydroxy-2-methyl-N-(3-methyl-4-nitrophenyl)-3-(3-methyl-4-nitrophenylamino)propionamide 2-Hydroxy-2-methyl-N-(3-methyl-4-nitrophenyl)-3-(3-methyl-4-nitrophenylamino)propionamide was prepared as described in Example 52 starting from 1,2-epoxy-2-methyl-N-[3-methyl-4-nitrophenyl]-2-propanamide. $^1$H-NMR (400 MHz, DMSO-$d_6$): 1.62 (3H, s), 2.54 (3H, s), 2.60 (3H, s), 3.41 (1H, dd, J=13.6 Hz, J=6.0 Hz), 3.83 (1H, dd, J=13.6 Hz, J=6.9 Hz), 4.81 (1H, t, J=6.3 Hz), 6.46 (1H, d, 2.1 Hz), 6.51 (1H, dd, J=9.1 Hz, J=2.5 Hz), 7.54 (1H, dd, J=8.9 Hz, J=2.2 Hz), 7.59 (1H, d, J=1.8 Hz), 7.97 (1H, d, J=9.0 Hz), 8.02 (1H, d, J=8.9 Hz), 8.96 (1H, s).

Example 91

3-[4-(3,3-dimethylureido)-3-fluorophenoxy]-2-hydroxy-2-methyl-N-(3-methyl-4-nitrophenyl)propionamide a) 3-(2-fluoro-4-hydroxyphenyl)-1,1-dimethylurea

4-Amino-3-fluorophenol (0.47 g; 3.0 mmol) was dissolved in 15 ml of dry THF under nitrogen, cooled to 0° C. and N,N'-dimethylcarbamyl chloride (0.28 ml; 3.0 mmol) was added dropwise. The reaction was allowed to heat to room temperature and then refluxed for 4 hours. The reaction was cooled again to 0° C. and 0.2 ml of water was added and the reaction filtered. The mother liquor was evaporated, dissolved in 25 ml of EtOAc, washed with 10 ml of 1M $Na_2CO_3$, 10 ml of water and dried over $Na_2SO_4$. The product was purified by chromatography (EtOAc:toluene 1:1). $^1$H NMR (400 MHz, DMSO-$d_6$): 2.88 (6H, s), 6.48-6.58 (2H, m), 7.02-7.10 (1H, m), 9.65 (1H, s).

b) 3-[4-(3,3-dimethylureido)-3-fluorophenoxy]-2-hydroxy-2-methyl-N-(3-methyl-4-nitrophenyl)propionamide 3-[4-(3,3-dimethylureido)-3-fluorophenoxy]-2-hydroxy-2-methyl-N-(3-methyl-4-nitrophenyl)propionamide was prepared as described in Example 1 from 3-(2-fluoro-4-hydroxyphenyl)-1,1-dimethylurea and 1,2-epoxy-2-methyl-N-[3-methyl-4-nitrophenyl]-2-propanamide. $^1$H NMR (400 MHz, DMSO-$d_6$): 1.42 (3H, s), 2.53 (3H, s), 2.88 (6H, s), 3.96 (1H, d, J=9.7 Hz), 4.21 (1H, d, J=9.7 Hz), 6.25 (1H, s), 6.68 (1H, dd, J=8.8 Hz, J=2.4 Hz), 6.81 (1H, dd, J=12.3 Hz, J=2.7 Hz), 7.10-7.30 (1H, m), 7.86 (1H, s), 7.88 (1H, dd, J=9.1 Hz, J=2.2 Hz), 7.93 (1H, d, J=1.9 Hz), 8.04 (1H, d, J=9.0 Hz), 10.15 (1H, s).

Example 92

3-(3-Fluoro-4-methanesulfonylaminophenoxy]-2-hydroxy-2-methyl-N-(3-methyl-4-nitrophenyl)propionamide a) N-(2-Fluoro-4-hydroxyphenyl)methanesulfonamide

4-Amino-3-fluorophenol (0.254 g; 2.0 mmol) was dissolved in 10 ml of dry pyridine under nitrogen and cooled to 0° C. Methanesulfonyl chloride (0.17 ml; 2.1 mmol) was added dropwise and stirred for three days at room temperature. The reaction was evaporated, 25 ml of toluene added and evaporated again. Toluene evaporation was repeated. Residue was dissolved in 25 ml of EtOAc, washed with 20 ml of water and evaporated to dryness to give red-brown solid N-(2-fluoro-4-hydroxyphenyl)methanesulfonamide. $^1$H NMR (400 MHz, DMSO-$d_6$): 2.93 (3H, s), 6.56-6.66 (2H, m), 7.14 (1H, t, J=9.0 Hz), 9.17 (1H, s), 9.98 (1H, s).

b) 3-(3-Fluoro-4-methanesulfonylaminophenoxy]-2-hydroxy-2-methyl-N-(3-methyl-4-nitrophenyl)propionamide 3-(3-Fluoro-4-methanesulfonylaminophenoxy]-2-hydroxy-2-methyl-N-(3-methyl-4-nitrophenyl)propionamide was prepared as in Example 1 starting from 4-amino-2-fluorophenol and 1,2-epoxy-2-methyl-N-[3-methyl-4-nitrophenyl]-2-propanamide. $^1$H NMR (400 MHz, DMSO-$d_6$): 1.43 (3H, s), 2.53 (3H, s), 2.92 (3H, s), 3.99 (1H, d, J=9.8 Hz), 4.24 (1H, d, J=9.8 Hz), 6.25 (1H, s), 6.76 (1H, dd, J=8.9 Hz, J=2.0 Hz), 6.93 (1H, dd, J=12.1 Hz, J=2.7 Hz), 7.23 (1H, t, J=9.1 Hz), 7.88 (1H, dd, J=9.0 Hz, J=2.2 Hz), 7.93 (1H, d, J=1.9 Hz), 8.04 (1H, d, J=9.0 Hz), 9.29 (1H, s), 10.16 (1H, s).

Example 93

3-[4-(2-aminoacetylamino)-3-fluorophenoxy]-2-hydroxy-2-methyl-N-(3-methyl-4-nitrophenyl)propionamide a) [(2-Fluoro-4-hydroxyphenylcarbamoyl)carbamicacid-tert-butylester tert-Butoxycarbonylamino acetic acid (=Boc-glycine) (0.256 g; 2.0 mmol) was dissolved in 10 ml of $CH_2Cl_2$ under nitrogen and cooled to 0° C. DCC (0.412 g; 2.0 mmol) was added and allowed to heat to room temperature. 4-Amino-3-fluoro-phenol (0.350 g; 2.0 mmol) was added in 10 ml of $CH_2Cl_2$ followed with 5 ml of THF. The reaction was stirred for 2 hours at room temperature, refluxed for 2 hours and stirred overnight at room temperature. The reaction was evaporated, dissolved in 30 ml of EtOAc and some heptane was added in order to precipitate out the residues (DHU) formed from DCC. The precipitate was filtered and washed with heptane. A mother liquor was evaporated, dissolved in 10 ml of EtOAc and 2 ml of toluene was added dropwise to give a precipitation. After filtration the filtrate was evaporated to give [(2-fluoro-4-hydroxyphenylcarbamoyl)carbamicacid-tert-butylester. $^1$H-NMR (400 MHz, DMSO-$d_6$): 1.39 (9H, s), 3.71 (2H, d, J=6.0 Hz), 6.52-6.65 (2H, m), 7.00-7.07 (1H, m), 7.41-7.49 (1H, m), 9.34 (1H, s), 9.74 (1H, s).

b) ({2-Fluoro-4-[2-hydroxy-2-(3-methyl-4-nitrophenylcarbamoyl}methyl)-carbamicacid-tert-butylester ({2-Fluoro-4-[2-hydroxy-2-(3-methyl-4-nitrophenylcarbamoyl}methyl)-carbamicacid-tert-butylester was prepared as described in Example 1 starting from [(2-fluoro-4-hydroxyphenylcarbamoyl)-carbamicacid-tert-butylester and 1,2-epoxy-2-methyl-N-[3-methyl-4-nitrophenyl]-2-propanamide. $^1$H-NMR (400 MHz, DMSO-$d_6$): 1.39 (9H, s), 1.43 (3H, s), 2.53 (3H, s), 3.73 (2H, d, J=5.4 Hz), 3.97 (1H, d, J=9.8 Hz), 4.22 (1H, d, J=9.8 Hz), 6.24 (1H, s), 6.74 (1H, d, J=9.3 Hz), 6.89 (1H, d, J=12.0 Hz), 7.00-7.10 (1H, m), 7.60 (1H, t, J=8.9 Hz), 7.88 (1H, d, J=9.0 Hz), 7.93 (1H, s), 8.04 (1H, d, J=9.0 Hz), 9.46 (1H, s), 10.15 (1H, s).

c) 3-[4-(2-aminoacetylamino)-3-fluorophenoxy]-2-hydroxy-2-methyl-N-(3-methyl-4-nitrophenyl)propionamide ({2-Fluoro-4-[2-hydroxy-2-(3-methyl-4-nitrophenylcarbamoyl}methyl)-carbamicacid-tert-butylester (0.160 g; 0.3 mmol) was dissolved in 5 ml of $CH_2Cl_2$ under nitrogen and cooled to 0° C. Trifluoroaceticacid (0.5 ml) was added dropwise and the reaction allowed to warm to room temperature followed with stirring for 2 hours at room temperature. The reaction was evaporated to dryness, the residue was dissolved in 25 ml of EtOAc and washed with 10 ml of water. Toluene (25 ml) was added and evaporated to dryness carefully to give 3-[4-(2-aminoacetylamino)-3-fluorophenoxy]-2-hydroxy-2-methyl-N-(3-methyl-4-nitrophenyl)propionamide. $^1$H-NMR (400 MHz, DMSO-$d_6$): 1.43 (3H, s), 2.53 (3H, s), 3.75-3.85 (2H, m), 3.98 (1H, d, J=9.1 Hz), 4.24 (1H, d, J=9.3 Hz), 6.25 (1H, s), 6.78 (1H, d, J=9.0 Hz), 6.95 (1H, d, J=13.0 Hz), 7.60-7.72 (1H, m), 7.88 (1H, d, J=8.8 Hz), 7.93 (1H, s), 8.00-8.15 (4H, m), 10.05 (1H, s), 10.12 (1H, s).

The invention claimed is:
1. A compound of formula (I)

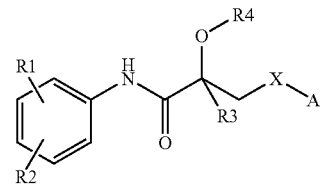

wherein
R1 is $(C_1-C_7)$alkyl, hydroxy$(C_1-C_7)$alkyl or —$(CH_2)_n$—CHO, wherein n is 0-6;
R2 is nitro, cyano or halogen;
R3 is hydrogen, $(C_1-C_7)$alkyl or halo$(C_1-C_7)$alkyl;
R4 is hydrogen, $(C_1-C_7)$alkyl, $COR_{10}$ or $SO_2R_{13}$;
X is O or NH;
A is a group selected from:

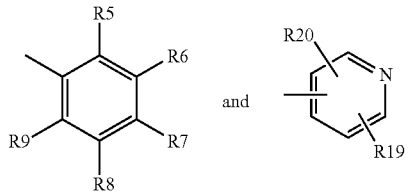

wherein $R_5$, $R_6$, $R_7$, $R_8$ and $R_9$ are independently selected from hydrogen, halogen, nitro, cyano, $(C_1-C_7)$alkyl, halo$(C_1-C_7)$alkyl, cyano$(C_1-C_7)$alkyl, amino, mono- or di$(C_1-C_7)$alkylamino, amino$(C_1-C_7)$alkyl, hydroxy$(C_1-C_7)$alkyl, $(C_1-C_7)$alkoxy$(C_1-C_7)$alkyl, —$NHCOR_{10}$, —$N(COR_{10})_2$, —$COR_{11}$, —$OR_{12}$, —$OSO_2R_{13}$, —$SO_2R_{14}$, —$NHSO_2R_{13}$, $SR_{15}$ and an imide ring; or
$R_5$ and $R_6$, $R_6$ and $R_7$, $R_7$ and $R_8$, or $R_8$ and $R_9$ form, together with any of the ring atom(s) to which they are attached, a condensed 5 to 7 membered aliphatic or aromatic carbocyclic ring or a condensed 5 to 7 membered heterocyclic ring containing 1 to 3 heteroatom (s) selected from N, O and S;
$R_{10}$ and $R_{11}$ are independently selected from $(C_1-C_7)$alkyl, $(C_2-C_7)$alkenyl, halo$(C_1-C_7)$alkyl, amino$(C_1-C_7)$alkyl, mono- or di($C_1$-$C_7$)alkylamino($C_1$-$C_7$)alkyl, ($C_6$-$C_{10}$) aryl, —N($R_{16}$)$_2$ and —O$R_{17}$;

$R_{12}$ and $R_{15}$ are independently selected from hydrogen, ($C_1$-$C_7$)alkyl, ($C_2$-$C_7$)alkenyl, halo($C_1$-$C_7$)alkyl, amino ($C_1$-$C_7$)alkyl, mono- or di($C_1$-$C_7$)alkylamino($C_1$-$C_7$) alkyl, ($C_6$-$C_{10}$)aryl, and —CO$R_{18}$;

$R_{13}$ and $R_{14}$ are independently selected from ($C_1$-$C_7$)alkyl or ($C_2$-$C_7$)alkenyl, halo($C_1$-$C_7$)alkyl and ($C_6$-$C_{10}$)aryl;

$R_{16}$ and $R_{17}$ are independently selected from hydrogen, ($C_1$-$C_7$)alkyl, ($C_2$-$C_7$)alkenyl, halo($C_1$-$C_7$)alkyl, amino ($C_1$-$C_7$)alkyl and ($C_6$-$C_{10}$)aryl;

$R_{18}$ is ($C_1$-$C_7$)alkyl, ($C_2$-$C_7$)alkenyl, halo($C_1$-$C_7$)alkyl or ($C_6$-$C_{10}$)aryl;

$R_{19}$ and $R_{20}$ are independently selected from hydrogen, halogen, ($C_1$-$C_7$)alkyl and ($C_2$-$C_7$)alkenyl;

and wherein each aryl or ring residue defined above may be substituted;

or a pharmaceutically acceptable salt or ester thereof.

2. A compound according to claim 1, wherein $R_4$ is hydrogen and $R_3$ is methyl.

3. A compound according to claim 1, wherein X is O.

4. A compound according to claim 1, wherein $R_1$ is methyl or hydroxymethyl and $R_2$ is nitro or cyano.

5. A compound according to claim 1, wherein $R_5$, $R_6$, $R_7$, $R_8$ and $R_9$ are independently selected from hydrogen, halogen, nitro, cyano, ($C_1$-$C_7$)alkyl, ($C_1$-$C_7$)alkoxy, halo($C_1$-$C_7$)alkyl, hydroxy($C_1$-$C_7$)alkyl and —NHCO$R_{10}$, wherein $R_{10}$ is ($C_1$-$C_7$)alkyl, halo($C_1$-$C_7$)alkyl, hydroxy or ($C_1$-$C_7$)alkoxy.

6. A compound according to claim 5, wherein at least one of $R_5$, $R_6$, $R_7$, $R_8$ and $R_9$ is a halogen.

7. A compound according to claim 6, wherein at least two of $R_5$, $R_6$, $R_7$, $R_8$ and $R_9$ are selected from halogen, cyano and acetamido.

8. A pharmaceutical composition comprising a compound as claimed in claim 1 and a pharmaceutically acceptable carrier.

9. A method of hormonal therapy, comprising administering to a subject in need thereof a therapeutically effective amount of a compound as claimed in claim 1.

10. A method for the treatment of an androgen receptor dependent condition, comprising administering to a subject in need thereof a therapeutically effective amount of a compound as claimed in claim 1.

11. A method according to claim 9, comprising administering a therapeutically effective amount of the compound orally.

* * * * *